(12) United States Patent
Presta

(10) Patent No.: US 8,691,532 B2
(45) Date of Patent: Apr. 8, 2014

(54) NUCLEIC ACIDS ENCODING ENGINEERED ANTI-IL-23R ANTIBODIES

(71) Applicant: Leonard G. Presta, San Francisco, CA (US)

(72) Inventor: Leonard G. Presta, San Francisco, CA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/671,371

(22) Filed: Nov. 7, 2012

(65) Prior Publication Data

US 2013/0064817 A1    Mar. 14, 2013

Related U.S. Application Data

(63) Continuation of application No. 13/399,847, filed on Feb. 17, 2012, now Pat. No. 8,309,085, which is a continuation of application No. 12/526,544, filed as application No. PCT/US2008/002534 on Feb. 26, 2008, now Pat. No. 8,119,133.

(60) Provisional application No. 60/892,104, filed on Feb. 28, 2007, provisional application No. 60/945,183, filed on Jun. 20, 2007.

(51) Int. Cl.
*C12N 15/09* (2006.01)

(52) U.S. Cl.
USPC .......... 435/69.6; 435/235.1; 435/252.1; 435/325; 536/23.53; 530/388.22; 530/350

(58) Field of Classification Search
None
See application file for complete search history.

(56) References Cited

U.S. PATENT DOCUMENTS

| | | | |
|---|---|---|---|
| 6,309,636 | B1 | 10/2001 | do Couto et al. |
| 6,495,667 | B1 | 12/2002 | Bazan |
| 6,756,481 | B2 | 6/2004 | Chirica et al. |
| 7,332,156 | B2 | 2/2008 | Bowman et al. |
| 7,422,743 | B2 | 9/2008 | Chirica et al. |
| 7,575,741 | B2 | 8/2009 | Bowman et al. |
| 2003/0009018 | A1 | 1/2003 | Maeda et al. |
| 2003/0082734 | A1 | 5/2003 | Dowling et al. |
| 2004/0152161 | A1 | 8/2004 | Cosman et al. |

FOREIGN PATENT DOCUMENTS

| | | |
|---|---|---|
| WO | WO 00/53631 | 9/2000 |
| WO | WO 01/18051 | 3/2001 |
| WO | WO 2004/058178 | 7/2004 |
| WO | WO 2004/071517 | 8/2004 |
| WO | WO 2004/081190 | 9/2004 |
| WO | WO 2005/047324 | 5/2005 |
| WO | WO 2005/047326 | 5/2005 |
| WO | WO 2005/052157 | 6/2005 |

OTHER PUBLICATIONS

Barbie and Lefranc (1998) *Experimental and Clinical Immunogenetics* 15:171-183, "The Human Immunoglobulin Kappa Variable (IGKV) Genes and Joining (IGKJ) Segments".
Bischoff & Kolbe (1994) *J. Chromatogr. B Biomed. Appl.* 662(2):261-278, "Deamidation of asparagine and glutamine residues in proteins and peptides: structural determinants and analytical methodology".
Bowman et al. (2006) *Curr. Opin. Infect. Dis.* 19(3):245-252, "Rationale and safety of anti-interleukin-23 and anti-interleukin-17A therapy".
Duerr et al. (2006) *Science* 314:1461-1463, "A genome-wide association study identifies IL23R as an inflammatory bowel disease gene".
Elkins et al. (2002) *Infection Immunity* 70:1936-1948, "In vivo clearance of an intracellular bacterium, *Francisella tularensis* LVS, is dependent on the p40 subunit of interleukin-12 (IL-12) but not on IL-12 p70".
Frucht (2002) *Sci STKE* 2002, E1-E3, "IL-23: a cytokine that acts on memory T cells".
Lefranc (2001) *Experimental and Clinical Immunogenetics* 18:100-116, "Nomenclature of the Human Immunoglobulin Heavy (IGH) Genes".
Lefranc (2001) *Experimental and Clinical Immunogenetics* 18:161-174, "Nomenclature of the Human Immunoglobulin Kappa (IGK) Genes".
Maccallum et al. (1996) *J. Mol. Biol.* 262:732-745 "Antibody-antigen Interactions: Contact Analysis and Binding Site Topography".
Oppmann et al. (2000) *Immunity* 13:715-725, "Novel p19 protein engages IL-12p40 to form a cytokine, IL-23, with biological activities similar as well as distinct from IL-12".
Padlan et al. (1989) *Proc. Natl. Acad. Sci. USA* 86:5938-5942 "Structure of an antibody-antigen complex: Crystal structure of the HyHEL-10 Fab-lysozyme complex".
Parham et al. (2002) *J. Immunol.* 168(11):5699-5708, "A receptor for the heterodimeric cytokine IL-23 is composed of IL-12R1 and a novel cytokine receptor subunit, IL-23R".
R&D Systems Catalog (2010) "Human IL-23R Antibody; Monoclonal Mouse IgG2B Clone #218213", Catalog Part No. MAB14001.
Tramontano et al. (1990) *J. Mol. Biol.* 215(1):175-182, "Framework residue 71 is a major determinant of the position and conformation of the second hypervariable region in the VH domains of immunoglobulins".
Wiekowski et al. (2001) *J. Immunol.* 166:7563-7570, "Ubiquitous transgenic expression of the IL-23 subunit p19 induces multiorgan inflammation, runting, infertility, and premature death".

*Primary Examiner* — Dong Jiang
(74) *Attorney, Agent, or Firm* — Gregory R. Bellomy

(57) ABSTRACT

Antibodies to human IL-23R are provided, as well as uses thereof, e.g. in treatment of inflammatory, autoimmune, and proliferative disorders.

17 Claims, 2 Drawing Sheets

```
                                             ----CDRH1---
r41F11    EVQLVESGGGLVQPGRSLKLSCVAS  GFTFNNSW--MT  WIRQAPGKGLECVA
r8B10     EVKLVESGGGLEQPKGSLKLSCTVS  GFDFNSYG--MS  WVRQAPGKGLDLVA
hu8B10    QVQLVESGGGVVQPGRSLRLSCAAS  GFDFNSYG--MS  WVRQAPGKGLEWVA
r3C11     QVTLKESGPGILQPSQTLSLTCTFS  GFSLSTYGMGVG  WIRQPSGKGLEWLA
m20E5     QVPLQQPGTELVKPGASVKLSCKAS  GYTFTSYW--IH  WVKQRPEQGLEWIG
m20D7     QIQLVQSGPELKKPGETVKISCKAS  GYTFTNYA--MN  WVKQAPGKGLKWMG
hu20D7-a  QVQLVQSGAEVKKPGASVKVSCKAS  GYTFTNYA--MN  WVRQAPGQGLEWMG
hu20D7-b  QVQLVQSGAEVKKPGASVKVSCKAS  GYTFTNYA--MN  WVRQAPGQGLEWMG
hu20D7-c  QVQLVQSGAEVKKPGASVKVSCKAS  GYTFTNYA--MN  WVRQAPGQGLEWMG

-------CDRH2-------
r41F11    SITNTGG--STYYPDSVKG  RFTISRDNAKSTLYLQMNSLRSEDTATYYCSR
r8B10     DINSKSYNYATYYADSVKD  RFTISRDDSQSMVYLEMDNLKTEDTALYYCTV
hu8B10    DINSKSYNYATYYADSVKD  RFTISRDNSKNTLYLQMNSLRAEDTAVYYCAR
r3C11     NIWWDDD---KYYNPSLKN  RLTISKDTSNNQAFLKITNVDTADTATYYCAR
m20E5     EIDPSDS--YTYYNQKFKD  KATLTVDKSSTTAFLQLSSLTSEDSAVYYCAR
m20D7     WINTYTG--EPTYSDDFKG  RFAFSLETSANTAYLQINNLKNEDTAAYFCTR
hu20D7-a  WINTYTG--EPTYSDDFKG  RVTMTTDTSTSTAYMELRSLRSDDTAVYYCAR
hu20D7-b  WINTYTG--EPTYSDDFKG  RVTMTLDTSTSTAYMELRSLRSDDTAVYYCAR
hu20D7-c  WINTYTG--EPTYSDDFKG  RVTFTLDTSTSTAYMELRSLRSDDTAVYYCAR

------CDRH3-------
r41F11    EDNS----------GYDY  WGQGVMVTVSS
r8B10     HHSD----------YFEY  WGQGVMVTVSS
hu8B10    HHSD----------YFEY  WGQGTLVTVSS
r3C11     IDAHPMGITTPDYYVVDA  WGQGASVTVSS
m20E5     SLYDYD--------GVPD  WGQGTLVTVSA
m20D7     GGGYDED-------YFDY  WGQGTTLTVSS
hu20D7-a  GGGYDED-------YFDY  WGQGTLVTVSS
hu20D7-b  GGGYDED-------YFDY  WGQGTLVTVSS
hu20D7-c  GGGYDED-------YFDY  WGQGTLVTVSS
```

Figure 1

```
                                    ------CDRL1------
r41F11       DIQMTQSPASLSASLGETVTIEC LASE------DIYSNLA
r8B10        DIQMTQSPASLSASLGETVSIEC LASE------DIYNNLA
hu8B10       DIQMTQSPSSLSASVGDRVTITC LASE------DIYNNLA
r3C11        DIVMTQSPTSMSISLGDRVTMNC KASQ------NVGSNVD
m20E5        DILMTQSPSSMSVSLGDTVSITC HASQ------GIDNNIG
m20D7        DIVMTQSPSSLAMSVGQKVTMNC KSSQSLFNSINQKTYLA
hu20D7-IV    DIVMTQSPDSLAVSLGERATINC KSSQSLFNSINQKTYLA
hu20D7-II-a  DIVMTQSPLSLPVTPGEPASISC KSSQSLFNSINQKTYLA
hu20D7-II-b  DIVMTQSPLSLPVTPGEPASISC KSSQSLFNTINQKTYLA

-CDRL2-
r41F11       WYQQKPGKSPQLLIY YANSLND GVPSRFSGSGSGT
r8B10        WYQQKPGKSPQLLIY HASSLQD GVPSRFSGSGSGT
hu8B10       WYQQKPGKAPKLLIY HASSLQD GVPSRFSGSGSGT
r3C11        WYQQKTGQSPKLLIY KASNRYT GVPDRFTGSGSGT
m20E5        WLQQKPGKSFKGLIY HGTNLED GVPSRFSGSGSGT
m20D7        WYQQRPGQSPKLLVY FASTRES GVPDRFIGSGSGT
hu20D7-IV    WYQQKPGQPPKLLIY FASTRES GVPDRFSGSGSGT
hu20D7-II-a  WYLQKPGQSPQLLIY FASTRES GVPDRFSGSGSGT
hu20D7-II-b  WYLQKPGQSPQLLIY FASTRES GVPDRFSGSGSGT

--CDRL3--
r41F11       QYSLKINSLQSEDVSIYFC QQNYYSPPT FGGGTKLELKR
r8B10        QYSLKINSLESEDAATYFC LQDSEYPPT FGGGTKLELKR
hu8B10       DFTLTISSLQPEDFATYYC LQDSEYPPT FGQGTKVEIKR
r3C11        DFTFTISNMQAEDLSVYYC MQSNSYPLT FGSGTKLEIKR
m20E5        DYSLTISSLESEDFADYYC VQYAQFPFT FGGGTKLEIRR
m20D7        DFTLTINSVQAEDLADYFC QQHYDTPWT FGGGTKLEIKR
hu20D7-IV    DFTLTISSLQAEDVAVYYC QQHYDTPWT FGQGTKVEIKRT
hu20D7-II-a  DFTLKISRVEAEDVGVYYC QQHYDTPWT FGQGTKVEIKRT
hu20D7-II-b  DFTLKISRVEAEDVGVYYC QQHYDTPWT FGQGTKVEIKRT
```

Figure 2

NUCLEIC ACIDS ENCODING ENGINEERED ANTI-IL-23R ANTIBODIES

This application is a Continuation of U.S. patent application Ser. No. 13/399,847, filed Feb. 17, 2012, now U.S. Pat. No. 8,309,085, which is a Continuation of U.S. patent application Ser. No. 12/526,544, filed Feb. 5, 2010, now U.S. Pat. No. 8,119,133, issued on Feb. 21, 2012, which is a 371 of PCT Patent Application No. PCT/US08/02534, filed Feb. 26, 2008, which claims benefit of U.S. Provisional Patent Application Nos. 60/945,183, filed Jun. 20, 2007, and 60/892,104, filed Feb. 28, 2007, each of which is hereby incorporated by reference in its entirety herein.

FIELD OF THE INVENTION

The present invention relates generally to antibodies specific for interleukin-23R (IL-23R) and uses thereof. More specifically, the invention relates to humanized antibodies that recognize human IL-23R and modulate its activity, particularly in inflammatory, autoimmune and proliferative disorders.

BACKGROUND OF THE INVENTION

The immune system functions to protect individuals from infective agents, e.g., bacteria, multi-cellular organisms, and viruses, as well as from cancers. This system includes several types of lymphoid and myeloid cells such as monocytes, macrophages, dendritic cells (DCs), eosinophils, T cells, B cells, and neutrophils. These lymphoid and myeloid cells often produce signaling proteins known as cytokines The immune response includes inflammation, i.e., the accumulation of immune cells systemically or in a particular location of the body. In response to an infective agent or foreign substance, immune cells secrete cytokines which, in turn, modulate immune cell proliferation, development, differentiation, or migration. Immune response can produce pathological consequences, e.g., when it involves excessive inflammation, as in the autoimmune disorders. See, e.g., Abbas et al. (eds.) (2000) *Cellular and Molecular Immunology*, W.B. Saunders Co., Philadelphia, Pa.; Oppenheim and Feldmann (eds.) (2001) *Cytokine Reference*, Academic Press, San Diego, Calif.; von Andrian and Mackay (2000) *New Engl. J. Med.* 343:1020-1034; Davidson and Diamond (2001) *New Engl. J. Med.* 345:340-350.

Interleukin-12 (IL-12) is a heterodimeric molecule composed of p35 and p40 subunits. Studies have indicated that IL-12 plays a critical role in the differentiation of naïve T cells into T-helper type 1 CD4$^+$ lymphocytes that secrete IFNγ. It has also been shown that IL-12 is essential for T cell dependent immune and inflammatory responses in vivo. See, e.g., Cua et al. (2003) *Nature* 421:744-748. The IL-12 receptor is composed of IL-12Rβ1 and IL-12Rβ2 subunits.

Interleukin-23 (IL-23) is a heterodimeric cytokine comprised of two subunits, p19 which is unique to IL-23, and p40, which is shared with IL-12. The p19 subunit is structurally related to IL-6, granulocyte-colony stimulating factor (G-CSF), and the p35 subunit of IL-12. IL-23 mediates signaling by binding to a heterodimeric receptor, comprised of IL-23R and IL-12Rβ1, which is shared by the IL-12 receptor. See Parham et al. (2000) *J. Immunol.* 168:5699. IL-12 receptor is a complex of IL-12Rβ1 and IL-12Rβ2 subunits. See Presky et al. (1996) *Proc. Nat'l Acad. Sci. USA* 93:14002.

A number of early studies demonstrated that the consequences of a genetic deficiency in p40 (p40 knockout mouse; p40KO mouse) were more severe than those found in a p35KO mouse. Some of these results were eventually explained by the discovery of IL-23, and the finding that the p40KO prevents expression of not only IL-12, but also of IL-23 (see, e.g., Oppmann et al. (2000) *Immunity* 13:715-725; Wiekowski et al. (2001) *J. Immunol.* 166:7563-7570; Parham et al. (2002) *J. Immunol.* 168:5699-708; Frucht (2002) *Sci STKE* 2002, E1-E3; Elkins et al. (2002) *Infection Immunity* 70:1936-1948).

Recent studies, through the use of p40 KO mice, have shown that blockade of both IL-23 and IL-12 is an effective treatment for various inflammatory and autoimmune disorders. However, the blockade of IL-12 through p40 appears to have various systemic consequences such as increased susceptibility to opportunistic microbial infections. Bowman et al. (2006) *Curr. Opin. Infect. Dis.* 19:245.

IL-23R has been implicated as a critical genetic factor in the inflammatory bowel disorders Crohn's disease and ulcerative colitis. Duerr et al. (2006) *Science* 314:1461. A genome-wide association study found that the gene for IL-23R was highly associated with Crohn's disease, with an uncommon coding variant (Arg381Gln) conferring strong protection against the disease. This genetic association confirms prior biological findings (Yen et al. (2006) *J. Clin. Investigation* 116:1218) suggesting that IL-23 and its receptor are promising targets for new therapeutic approaches to treating IBD.

Therapeutic antibodies may be used to block cytokine activity. The most significant limitation in using antibodies as a therapeutic agent in vivo is the immunogenicity of the antibodies. As most monoclonal antibodies are derived from rodents, repeated use in humans results in the generation of an immune response against the therapeutic antibody. Such an immune response results in a loss of therapeutic efficacy at a minimum and a potential fatal anaphylactic response at a maximum. Initial efforts to reduce the immunogenicity of rodent antibodies involved the production of chimeric antibodies, in which mouse variable regions were fused with human constant regions. Liu et al. (1987) *Proc. Natl. Acad. Sci. USA* 84:3439-43. However, mice injected with hybrids of human variable regions and mouse constant regions develop a strong anti-antibody response directed against the human variable region, suggesting that the retention of the entire rodent Fv region in such chimeric antibodies may still result in unwanted immunogenicity in patients.

It is generally believed that complementarity determining region (CDR) loops of variable domains comprise the binding site of antibody molecules. Therefore, the grafting of rodent CDR loops onto human frameworks (i.e., humanization) was attempted to further minimize rodent sequences. Jones et al. (1986) *Nature* 321:522; Verhoeyen et al. (1988) *Science* 239: 1534. However, CDR loop exchanges still do not uniformly result in an antibody with the same binding properties as the antibody of origin. Changes in framework residues (FR), residues involved in CDR loop support, in humanized antibodies also are required to preserve antigen binding affinity. Kabat et al. (1991) *J. Immunol.* 147:1709. While the use of CDR grafting and framework residue preservation in a number of humanized antibody constructs has been reported, it is difficult to predict if a particular sequence will result in the antibody with the desired binding, and sometimes biological, properties. See, e.g., Queen et al. (1989) *Proc. Natl. Acad. Sci. USA* 86:10029, Gorman et al. (1991) *Proc. Natl. Acad. Sci. USA* 88:4181, and Hodgson (1991) *Biotechnology* (NY) 9:421-5. Moreover, most prior studies used different human sequences for animal light and heavy variable sequences, rendering the predictive nature of such studies questionable. Sequences of known antibodies have been used or, more typically, those of antibodies having known X-ray structures, antibodies NEW and KOL. See, e.g., Jones et al., supra; Verhoeyen et al., supra; and Gorman et al., supra. Exact sequence information has been reported for some humanized constructs.

The need exists for improved methods and compositions for the treatment of inflammatory, autoimmune, and proliferative disorders, e.g. by use of agents that prevent IL-23 signaling through its receptor, such as antagonists of the interaction of IL-23 and the IL-23 receptor. Alternatively such agents could be used to target cells expressing IL-23R for specific ablation. Preferably, such antagonists would have a high affinity for the target molecule, and would be able to block the IL-23 interaction with its receptor at relatively low doses. Preferably, such methods and compositions would be highly specific for IL-23, and not interfere with the activity of other cytokines, such as IL-12. Preferably, such methods and compositions would employ antagonists suitable for modification for the delivery of cytotoxic payloads to target cells, but also suitable for non-cytotoxic uses. Preferably, such methods and compositions would employ antibodies modified to limit their antigenicity when administered to a subject in need thereof.

SUMMARY OF THE INVENTION

The present invention meets these needs in the art and more by providing antagonists of human IL-23R, e.g. humanized anti-human IL-23R antibodies.

In one aspect the invention provides binding compounds, such as antibodies or fragments thereof, including humanized or chimeric recombinant antibodies, that bind to human IL-23R, comprising an antibody light chain variable domain, or antigen binding fragment thereof, having at least one, two or three CDRs selected from the group consisting of SEQ ID NOs: 26-40 and 52. In one embodiment, the binding compound of the present invention comprises a light chain variable domain comprising at least one CDRL1 selected from the group consisting of SEQ ID NOs: 26-30 and 52; at least one CDRL2 selected from the group consisting of SEQ ID NOs: 31-35; and at least one CDRL3 selected from the group consisting of SEQ ID NOs: 36-40.

In one embodiment, the binding compound comprises an antibody heavy chain variable domain, or antigen binding fragment thereof, having at least one, two or three CDRs selected from the group consisting of SEQ ID NOs: 11-25. In one embodiment, the binding compound of the present invention comprises a heavy chain variable domain comprising at least one CDRH1 selected from the group consisting of SEQ ID NOs: 11-15; at least one CDRH2 selected from the group consisting of SEQ ID NOs: 16-20; and at least one CDRH3 selected from the group consisting of SEQ ID NOs: 21-25.

In other embodiments the binding compound of the present invention comprises a light chain variable domain and a heavy chain variable domain, or the antigen binding fragments thereof, described in the preceding two paragraphs.

In some embodiments, the binding compound comprises a framework region, wherein the amino acid sequence of the framework region is all or substantially all of a human immunoglobulin amino acid sequence.

In some embodiments the light chain and/or heavy chain variable domains comprise a variant of one or more of the CDRs. In various embodiments the variant domain comprises up to 1, 2, 3, 4, 5, 6, 7, 8, 9, 10 or more conservatively modified amino acid residues relative to the sequence of the respective SEQ ID NOs. Conservative amino acid substitutions are provided at Table 1.

In some embodiments the light chain variable domain comprises a sequence selected from the group consisting of SEQ ID NOs: 48-49 and 53 or a variant thereof. In some embodiments the heavy chain variable domain comprises a sequence selected from the group consisting of SEQ ID NOs: 45-47. In various embodiments the variant variable domain comprises up to 1, 2, 3, 4, 5, 6, 7, 8, 9, 10, 15, 20, 30, 40 or 50 or more conservatively modified amino acid residues relative to the sequence of the respective SEQ ID NOs. In yet a further embodiment, the binding compound comprises a light chain variable domain and a heavy chain variable domain, or the antigen binding fragments thereof, described in this paragraph.

In other embodiments the binding compound of the present invention comprises a light chain variable domain, or an antigen binding fragment thereof, consisting essentially of a sequence selected from the group consisting of SEQ ID NOs: 48-49 and 53, and/or a heavy chain variable domain, or an antigen binding fragment thereof, consisting essentially of a sequence selected from the group consisting of SEQ ID NOs: 45-47.

In other embodiments the binding compound of the present invention comprises a light chain variable domain, or an antigen binding fragment thereof, having at least 50%, 75%, 80%, 85%, 90%, 95%, 98% or 99% sequence homology with a sequence selected from the group consisting of SEQ ID NOs: 6-10, 48-49 and 53, and/or a heavy chain variable domain, or an antigen binding fragment thereof, having at least 50%, 75%, 80%, 85%, 90%, 95%, 98% or 99% sequence homology with a sequence selected from the group consisting of SEQ ID NOs: 1-5 and 45-47.

In another embodiment the binding compound of the present invention comprises the antibody light chain variable domain of SEQ ID NOs: 49 or 53 and the antibody heavy chain variable domain of SEQ ID NO: 47, or an antigen binding fragment thereof. In a further embodiment, the binding compound comprises the light chain of SEQ ID NOs: 51 or 54 and the heavy chain of SEQ ID NO: 50, or an antigen binding fragment thereof. In yet a further embodiment, the binding compound is encoded by the nucleic acid sequences of SEQ ID NO: 55 (heavy chain) and SEQ ID NO: 56 (light chain). In a further embodiment, the binding compound comprises the light chain variable domain of SEQ ID NO: 58 and the heavy chain variable domain of SEQ ID NO: 57, or an antigen binding fragment thereof In one embodiment, the invention relates to antibodies that are able to block the binding of a binding compound of the present invention to human IL-23R in a cross-blocking assay. In various embodiments the antibody is able to block binding of human IL-23R to an antibody comprising the CDR sequences of antibodies 41F11, 8B10, 3C11, 20D7 (with or without the S32T sequence variation), 20E5, as disclosed herein. In other embodiments, the antibody is able to block binding of human IL-23R to the antibody deposited with ATCC under accession number PTA-7800, and/or the antibody deposited under ATCC accession number PTA-7801, in a cross-blocking assay. In another embodiment, the invention relates to binding compounds that are able to block IL-23R-mediated activity, such activities including but not limited to, binding IL-23, or mediating the proliferation or survival of $T_H17$ cells.

In some embodiments, the binding compound of the present invention comprises a humanized antibody comprising the CDRs, or variants thereof, selected from the CDRs of the antibodies disclosed herein, in combination with human germline light chain and heavy chain variable domain framework sequences in place of the rodent frameworks of the parental antibodies.

In some embodiments, the binding compound of the present invention further comprises a heavy chain constant region, wherein the heavy chain constant region comprises a γ1, γ2, γ3, or γ4 human heavy chain constant region or a variant thereof. In various embodiments the light chain constant region comprises a lambda or a kappa human light chain constant region.

In various embodiments the binding compounds of the present invention are polyclonal, monoclonal, chimeric, humanized or fully human antibodies or fragments thereof. The present invention also contemplates that the antigen binding fragment is an antibody fragment selected from the group consisting of Fab, Fab', Fab'-SH, Fv, scFv, F(ab')$_2$, and a diabody.

The present invention encompasses a method of suppressing an immune response in a human subject comprising administering to a subject in need thereof an antibody (or a antigen binding fragment thereof) specific for IL-23R in an amount effective to block IL-23 signaling. In some embodiments, the antibody specific for IL-23R is the humanized or chimeric antibody. In further embodiments, the immune response is an inflammatory response including arthritis, psoriasis, and inflammatory bowel disease. In other embodiments, the immune response is an autoimmune response, including multiple sclerosis, uveitis, systemic lupus erythematosus and diabetes. In another embodiment, the subject has cancer and the immune response is a Th17 response.

The present invention also contemplates administering an additional immunosuppressive or anti-inflammatory agent. The binding compounds of the present invention can be in a pharmaceutical composition comprising the binding compound, or antigen binding fragment thereof, in combination with a pharmaceutically acceptable carrier or diluent. In a further embodiment, the pharmaceutical composition further comprises an immunosuppressive or anti-inflammatory agent.

The present invention encompasses an isolated nucleic acid encoding the polypeptide sequence of an antibody embodiment of the binding compound of the present invention. The nucleic acid can be in an expression vector operably linked to control sequences recognized by a host cell transfected with the vector. Also encompassed is a host cell comprising the vector, and a method of producing a polypeptide comprising culturing the host cell under conditions wherein the nucleic acid sequence is expressed, thereby producing the polypeptide, and recovering the polypeptide from the host cell or medium.

In various embodiments, the invention relates to use of a binding compound of the present invention in the manufacture of medicaments for the treatment of disorders including, but not limited to, inflammatory disease, autoimmune disease, cancer, infectious disease (e.g. bacterial, mycobacterial, viral or fungal infection, including chronic infections), arthritis, psoriasis, inflammatory bowel disease, multiple sclerosis, uveitis, systemic lupus erythematosus and diabetes. In other embodiments the invention relates to compositions limited by the aforementioned uses.

In other embodiments the invention relates to pharmaceutical compositions comprising a binding compound of the present invention for treating disorders including, but not limited to, inflammatory disease, autoimmune disease, cancer, infectious disease (e.g. bacterial, mycobacterial, viral or fungal infection, including chronic infections), arthritis, psoriasis, inflammatory bowel disease, multiple sclerosis, uveitis, systemic lupus erythematosus and diabetes.

In some embodiments, the binding compound or pharmaceutical composition of the present invention induces a prolonged period of remission from disease symptoms in a subject, such that the dosing interval can be extended to much longer than the half-life of the binding compound in the subject, for example in the treatment of a relapsing-remitting disease. In various embodiments, the interval between one administration and another is 6-, 8-, 10-, 12-, 16-, 20-, 24-, 30-weeks or longer. In other embodiments a single administration is sufficient to permanently prevent relapses.

BRIEF DESCRIPTION OF THE DRAWINGS

FIG. 1 shows comparisons of rat ("r"), mouse ("m") and humanized ("hu") anti-human IL-23R antibody clone heavy chain variable domain sequences. Sequences are provided for clones r41F11, r8B10, hu8B10, r3C11, m20E5, m20D7, hu20D7-a, hu20D7-b and hu20D7-c. CDRs are indicated. Cross references to sequence identifiers in the Sequence Listing are provided at Table 4.

FIG. 2 shows comparisons of rat, mouse and humanized anti-human IL-23R antibody clone light chain variable domain sequences. Sequences are provided for clones r41F11, r8B10, hu8B10, r3C11, m20E5, m20D7, hu20D7-IV, hu20D7-II-a and hu20D7-II-b. CDRs are indicated. Cross references to sequence identifiers in the Sequence Listing are provided at Table 4.

DETAILED DESCRIPTION

As used herein, including the appended claims, the singular forms of words such as "a," "an," and "the," include their corresponding plural references unless the context clearly dictates otherwise. Table 4 below provides a listing of sequence identifiers used in this application. All references cited herein are incorporated by reference to the same extent as if each individual publication, database entry (e.g. Genbank sequences or GeneID entries), patent application, or patent, was specifically and individually indicated to be incorporated by reference. Citation of the references herein is not intended as an admission that the reference is pertinent prior art, nor does it constitute any admission as to the contents or date of these publications or documents.

I. Definitions

"Proliferative activity" encompasses an activity that promotes, that is necessary for, or that is specifically associated with, e.g., normal cell division, as well as cancer, tumors, dysplasia, cell transformation, metastasis, and angiogenesis.

"Administration" and "treatment," as it applies to an animal, human, experimental subject, cell, tissue, organ, or biological fluid, refers to contact of an exogenous pharmaceutical, therapeutic, diagnostic agent, or composition to the animal, human, subject, cell, tissue, organ, or biological fluid. "Administration" and "treatment" can refer, e.g., to therapeutic, pharmacokinetic, diagnostic, research, and experimental methods. Treatment of a cell encompasses contact of a reagent to the cell, as well as contact of a reagent to a fluid, where the fluid is in contact with the cell. "Administration" and "treatment" also means in vitro and ex vivo treatments, e.g., of a cell, by a reagent, diagnostic, binding composition, or by another cell. "Treatment," as it applies to a human, veterinary, or research subject, refers to therapeutic treatment, prophylactic or preventative measures, to research and diagnostic applications. "Treatment" as it applies to a human, veterinary, or research subject, or cell, tissue, or organ, encompasses contact of an agent with animal subject, a cell, tissue, physiological compartment, or physiological fluid. "Treatment of a cell" also encompasses situations where the agent contacts IL-23 receptor (IL-23R/IL-12Rβ1 heterodimer), e.g., in the fluid phase or colloidal phase, but also situations where the agonist or antagonist does not contact the cell or the receptor.

As used herein, the term "antibody" refers to any form of antibody that exhibits the desired biological activity. Thus, it is used in the broadest sense and specifically covers monoclonal antibodies (including full length monoclonal antibodies), polyclonal antibodies, multispecific antibodies (e.g., bispecific antibodies), chimeric antibodies, humanized antibodies, fully human antibodies, etc. so long as they exhibit the desired biological activity.

As used herein, the terms "IL-23R binding fragment," "binding fragment thereof" or "antigen binding fragment thereof" encompass a fragment or a derivative of an antibody that still substantially retains its biological activity of binding to IL-23R. In some embodiments, an antibody or antigen binding fragment thereof of the present invention inhibits IL-23 signaling via the IL-23 receptor, such inhibition being referred to herein as "IL-23R inhibitory activity." Because antagonists of IL-23R will have the biological activity of inhibiting IL-23 signaling, such antagonists are said (interchangeably) to inhibit IL-23R, inhibit IL-23, or inhibit both IL-23/IL-23R. The term "antibody fragment" or IL-23R binding fragment refers to a portion of a full length antibody, generally the antigen binding or variable region thereof. Examples of antibody fragments include Fab, Fab', F(ab')$_2$, and Fv fragments; diabodies; linear antibodies; single-chain antibody molecules, e.g., sc-Fv; and multispecific antibodies formed from antibody fragments. Typically, a binding fragment or derivative retains at least 10% of its IL-23R inhibitory activity. Preferably, a binding fragment or derivative retains at least 25%, 50%, 60%, 70%, 80%, 90%, 95%, 99% or 100% (or more) of its IL-23R inhibitory activity, although any binding fragment with sufficient affinity to exert the desired biological effect will be useful. It is also intended that, when specified, a IL-23R binding fragment can include variants having conservative amino acid substitutions that do not substantially alter its biologic activity.

The term "monoclonal antibody", as used herein, refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic epitope. In contrast, conventional (polyclonal) antibody preparations typically include a multitude of antibodies directed against (or specific for) different epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) Nature 256: 495, or may be made by recombinant DNA methods (see, e.g., U.S. Pat. No. 4,816,567). The "monoclonal antibodies" may also be isolated from phage antibody libraries using the techniques described in Clackson et al. (1991) Nature 352: 624-628 and Marks et al. (1991) J. Mol. Biol. 222: 581-597, for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity. U.S. Pat. No. 4,816,567; Morrison et al. (1984) Proc. Natl. Acad. Sci. USA 81: 6851-6855.

A "domain antibody" is an immunologically functional immunoglobulin fragment containing only the variable region of a heavy chain or the variable region of a light chain. In some instances, two or more V$_H$ regions are covalently joined with a peptide linker to create a bivalent domain antibody. The two V$_H$ regions of a bivalent domain antibody may target the same or different antigens.

A "bivalent antibody" comprises two antigen binding sites. In some instances, the two binding sites have the same antigen specificities. However, bivalent antibodies may be bispecific (see below).

As used herein, the term "single-chain Fv" or "scFv" antibody refers to antibody fragments comprising the V$_H$ and V$_L$ domains of antibody, wherein these domains are present in a single polypeptide chain. Generally, the Fv polypeptide further comprises a polypeptide linker between the V$_H$ and V$_L$ domains which enables the scFv to form the desired structure for antigen binding. For a review of scFv, see Pluckthun (1994) THE PHARMACOLOGY OF MONOCLONAL ANTIBODIES, vol. 113, Rosenburg and Moore eds. Springer-Verlag, New York, pp. 269-315.

The monoclonal antibodies herein also include camelized single domain antibodies. See, e.g., Muyldermans et al. (2001) Trends Biochem. Sci. 26:230; Reichmann et al. (1999) J. Immunol. Methods 231:25; WO 94/04678; WO 94/25591; U.S. Pat. No. 6,005,079). In one embodiment, the present invention provides single domain antibodies comprising two V$_H$ domains with modifications such that single domain antibodies are formed.

As used herein, the term "diabodies" refers to small antibody fragments with two antigen-binding sites, which fragments comprise a heavy chain variable domain (V$_H$) connected to a light chain variable domain (V$_L$) in the same polypeptide chain (V$_H$-V$_L$ or V$_L$-V$_H$). By using a linker that is too short to allow pairing between the two domains on the same chain, the domains are forced to pair with the complementary domains of another chain and create two antigen-binding sites. Diabodies are described more fully in, e.g., EP 404,097; WO 93/11161; and Holliger et al. (1993) Proc. Natl. Acad. Sci. USA 90: 6444-6448. For a review of engineered antibody variants generally see Holliger and Hudson (2005) Nat. Biotechnol. 23:1126-1136.

As used herein, the term "humanized antibody" refers to forms of antibodies that contain sequences from non-human (e.g., murine) antibodies as well as human antibodies. Such antibodies contain minimal sequence derived from non-human immunoglobulin. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. The prefix "hum", "hu" or "h" is added to antibody clone designations when necessary to distinguish humanized antibodies from parental rodent antibodies (although these same designations, depending on the context, may also indicate the human form of a particular protein). The humanized forms of rodent antibodies will generally comprise the same CDR sequences of the parental rodent antibodies, although certain amino acid substitutions may be included to increase affinity, increase stability of the humanized antibody, or for other reasons.

The antibodies of the present invention also include antibodies with modified (or blocked) Fc regions to provide altered effector functions. See, e.g., U.S. Pat. No. 5,624,821; WO2003/086310; WO2005/120571; WO2006/0057702; Presta (2006) *Adv. Drug Delivery Rev.* 58:640-656. Such modification can be used to enhance or suppress various reactions of the immune system, with possible beneficial effects in diagnosis and therapy. Alterations of the Fc region include amino acid changes (substitutions, deletions and insertions), glycosylation or deglycosylation, and adding multiple Fc. Changes to the Fc can also alter the half-life of antibodies in therapeutic antibodies. A longer half-life may result in less frequent dosing, with the concomitant increased convenience and decreased use of material. See Presta (2005) *J. Allergy Clin. Immunol.* 116:731 at 734-35.

The antibodies of the present invention also include antibodies with intact Fc regions that provide full effector functions, e.g. antibodies of isotype IgG1, which induce complement-dependent cytotoxicity (CDC) or antibody dependent cellular cytotoxicity (ADCC) in the a targeted cell. In some embodiments, the antibodies of the present invention are administered to selectively deplete IL-23R-positive cells from a population of cells. In one embodiment, this depletion of IL-23R-positive cells is the depletion of pathogenic Th17 cells. Depletion of such pathogenic T cell subset may result in sustained remission when effected in subjects suffering from a relapsing/remitting autoimmune disease.

The antibodies of the present invention also include antibodies conjugated to cytotoxic payloads, such as cytotoxic agents or radionuclides. Such antibody conjugates may be used in immunotherapy to selectively target and kill cells expressing IL-23R on their surface. Exemplary cytotoxic agents include ricin, vinca alkaloid, methotrexate, *Psuedomonas* exotoxin, saporin, diphtheria toxin, cisplatin, doxorubicin, abrin toxin, gelonin and pokeweed antiviral protein. Exemplary radionuclides for use in immunotherapy with the antibodies of the present invention include $^{125}$I, $^{131}$I, $^{90}$Y, $^{67}$Cu, $^{211}$At, $^{177}$Lu, $^{143}$Pr and $^{213}$Bi. See, e.g., U.S. Patent Application Publication No. 2006/0014225.

The term "fully human antibody" refers to an antibody that comprises human immunoglobulin protein sequences only. A fully human antibody may contain murine carbohydrate chains if produced in a mouse, in a mouse cell, or in a hybridoma derived from a mouse cell. Similarly, "mouse antibody" or "rat antibody" refer to an antibody that comprises only mouse or rat immunoglobulin sequences, respectively. A fully human antibody may be generated in a human being, in a transgenic animal having human immunoglobulin germline sequences, by phage display or other molecular biological methods.

As used herein, the term "hypervariable region" refers to the amino acid residues of an antibody that are responsible for antigen-binding. The hypervariable region comprises amino acid residues from a "complementarity determining region" or "CDR" (e.g. residues 24-34 (CDRL1), 50-56 (CDRL2) and 89-97 (CDRL3) in the light chain variable domain and residues 31-35 (CDRH1), 50-65 (CDRH2) and 95-102 (CDRH3) in the heavy chain variable domain (Kabat et al. (1991) Sequences of Proteins of Immunological Interest, 5th Ed. Public Health Service, National Institutes of Health, Bethesda, Md.) and/or those residues from a "hypervariable loop" (i.e. residues 26-32 (L1), 50-52 (L2) and 91-96 (L3) in the light chain variable domain and 26-32 (H1), 53-55 (H2) and 96-101 (H3) in the heavy chain variable domain (Chothia and Lesk (1987) *J. Mol. Biol.* 196: 901-917). As used herein, the term "framework" or "FR" residues refers to those variable domain residues other than the hypervariable region residues defined herein as CDR residues. The residue numbering above relates to the Kabat numbering system and does not necessarily correspond in detail to the sequence numbering in the accompanying Sequence Listing. Sequence variants in both the CDR and framework regions are contemplated, and may be represented as "XbbZ", in which amino acid "X" at position "bb" is replaced by amino acid "Z", and wherein X and Z are in either triple- or single-letter amino acid code, and position number "bb" is typically defined with respect to the numbering of a specific sequence disclosed in the Sequence Listing.

"Binding compound" refers to a molecule, small molecule, macromolecule, polypeptide, antibody or fragment or analogue thereof, or soluble receptor, capable of binding to a target. "Binding compound" also may refer to a complex of molecules, e.g., a non-covalent complex, to an ionized molecule, and to a covalently or non-covalently modified molecule, e.g., modified by phosphorylation, acylation, cross-linking, cyclization, or limited cleavage, that is capable of binding to a target. When used with reference to antibodies, the term "binding compound" refers to both antibodies and antigen binding fragments thereof "Binding" refers to an association of the binding compound with a target where the association results in reduction in the normal Brownian motion of the binding compound, in cases where the binding compound can be dissolved or suspended in solution. "Binding composition" refers to a molecule, e.g. a binding compound, in combination with a stabilizer, excipient, salt, buffer, solvent, or additive, capable of binding to a target.

"Conservatively modified variants" or "conservative substitution" refers to substitutions of amino acids are known to those of skill in this art and may often be made even in essential regions of the polypeptide without altering the biological activity of the resulting molecule. Such exemplary substitutions are preferably made in accordance with those set forth in Table 1 as follows:

TABLE 1

Exemplary Conservative Amino Acid Substitutions

| Original residue | Conservative substitution |
|---|---|
| Ala (A) | Gly; Ser |
| Arg (R) | Lys, His |
| Asn (N) | Gln; His |
| Asp (D) | Glu; Asn |
| Cys (C) | Ser; Ala |
| Gln (Q) | Asn |
| Glu (E) | Asp; Gln |
| Gly (G) | Ala |
| His (H) | Asn; Gln |
| Ile (I) | Leu; Val |
| Leu (L) | Ile; Val |
| Lys (K) | Arg; His |
| Met (M) | Leu; Ile; Tyr |
| Phe (F) | Tyr; Met; Leu |
| Pro (P) | Ala |
| Ser (S) | Thr |
| Thr (T) | Ser |
| Trp (W) | Tyr; Phe |
| Tyr (Y) | Trp; Phe |
| Val (V) | Ile; Leu |

Those of skill in this art recognize that, in general, single amino acid substitutions in non-essential regions of a polypeptide may not substantially alter biological activity. See, e.g., Watson et al. (1987) *Molecular Biology of the Gene*, The Benjamin/Cummings Pub. Co., p. 224 (4th Edition).

The phrase "consists essentially of," or variations such as "consist essentially of" or "consisting essentially of," as used throughout the specification and claims, indicate the inclusion of any recited elements or group of elements, and the optional inclusion of other elements, of similar or different nature than the recited elements, that do not materially change the basic or novel properties of the specified dosage regimen, method, or composition. As a non-limiting example, a binding compound that consists essentially of a recited amino acid sequence may also include one or more amino acids, including substitutions of one or more amino acid residues, that do not materially affect the properties of the binding compound.

"Effective amount" encompasses an amount sufficient to ameliorate or prevent a symptom or sign of the medical condition. Such an effective amount need not necessarily completely ameliorate or prevent such symptom or sign. Effective amount also means an amount sufficient to allow or facilitate diagnosis. An effective amount for a particular patient or veterinary subject may vary depending on factors such as the condition being treated, the overall health of the patient, the method route and dose of administration and the severity of side affects. See, e.g., U.S. Pat. No. 5,888,530. An effective amount can be the maximal dose or dosing protocol that avoids significant side effects or toxic effects. The effect will result in an improvement of a diagnostic measure or parameter by at least 5%, usually by at least 10%, more usually at least 20%, most usually at least 30%, preferably at least 40%, more preferably at least 50%, most preferably at least 60%, ideally at least 70%, more ideally at least 80%, and most ideally at least 90%, where 100% is defined as the diagnostic parameter shown by a normal subject. See, e.g., Maynard et al. (1996) *A Handbook of SOPs for Good Clinical Practice*, Interpharm Press, Boca Raton, Fla.; Dent (2001) *Good Laboratory and Good Clinical Practice*, Urch Publ., London, UK.

"Immune condition" or "immune disorder" encompasses, e.g., pathological inflammation, an inflammatory disorder, and an autoimmune disorder or disease. "Immune condition" also refers to infections, persistent infections, and proliferative conditions, such as cancer, tumors, and angiogenesis, including infections, tumors, and cancers that resist eradication by the immune system. "Cancerous condition" includes, e.g., cancer, cancer cells, tumors, angiogenesis, and precancerous conditions such as dysplasia.

"Inflammatory disorder" means a disorder or pathological condition where the pathology results, in whole or in part, from, e.g., a change in number, change in rate of migration, or change in activation, of cells of the immune system. Cells of the immune system include, e.g., T cells, B cells, monocytes or macrophages, antigen presenting cells (APCs), dendritic cells, microglia, NK cells, NKT cells, neutrophils, eosinophils, mast cells, or any other cell specifically associated with the immunology, for example, cytokine-producing endothelial or epithelial cells.

An "IL-17-producing cell" means a T cell that is not a classical TH1-type T cell or classical TH2-type T cell, referred to as $T_H17$ cells. $T_H17$ cells are discussed in greater detail at Cua and Kastelein (2006) *Nat. Immunol.* 7:557-559; Tato and O'Shea (2006) *Nature* 441:166-168; Iwakura and Ishigame (2006) *J. Clin. Invest.* 116:1218-1222. "IL-17-producing cell" also means a T cell that expresses a gene or polypeptide of Table 10B of U.S. Patent Application Publication No. 2004/0219150 (e.g., mitogen responsive P-protein; chemokine ligand 2; interleukin-17 (IL-17); transcription factor RAR related; and/or suppressor of cytokine signaling 3), where expression with treatment by an IL-23 agonist is greater than treatment with an IL-12 agonist, where "greater than" is defined as follows. Expression with an IL-23 agonist is ordinarily at least 5-fold greater, typically at least 10-fold greater, more typically at least 15-fold greater, most typically at least 20-fold greater, preferably at least 25-fold greater, and most preferably at least 30-fold greater, than with IL-12 treatment. Expression can be measured, e.g., with treatment of a population of substantially pure IL-17 producing cells. A Th17 response is an immune response in which the activity and/or proliferation of Th17 cells are enhanced, typically coupled with a repressed Th1 response.

Moreover, "IL-17-producing cell" includes a progenitor or precursor cell that is committed, in a pathway of cell development or cell differentiation, to differentiating into an IL-17-producing cell, as defined above. A progenitor or precursor cell to the IL-17 producing cell can be found in a draining lymph node (DLN). Additionally, "IL-17-producing cell" encompasses an IL-17-producing cell, as defined above, that has been, e.g., activated, e.g., by a phorbol ester, ionophore, and/or carcinogen, further differentiated, stored, frozen, desiccated, inactivated, partially degraded, e.g., by apoptosis, proteolysis, or lipid oxidation, or modified, e.g., by recombinant technology.

As used herein, the term "isolated nucleic acid molecule" refers to a nucleic acid molecule that is identified and separated from at least one contaminant nucleic acid molecule with which it is ordinarily associated in the natural source of the antibody nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

The expression "control sequences" refers to DNA sequences involved in the expression of an operably linked coding sequence in a particular host organism. The control sequences that are suitable for prokaryotes, for example, include a promoter, optionally an operator sequence, and a ribosome binding site. Eukaryotic cells are known to use promoters, polyadenylation signals, and enhancers.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers.

It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

As used herein, "polymerase chain reaction" or "PCR" refers to a procedure or technique in which minute amounts of a specific piece of nucleic acid, RNA and/or DNA, are amplified as described in, e.g., U.S. Pat. No. 4,683,195. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers can coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al. (1987) *Cold Spring Harbor Symp. Quant. Biol.* 51:263; Erlich, ed., (1989) PCR TECHNOLOGY (Stockton Press, N.Y.) As used herein, PCR is considered to be one, but not the only, example of a nucleic acid polymerase reaction method for amplifying a nucleic acid test sample comprising the use of a known nucleic acid as a primer and a nucleic acid polymerase to amplify or generate a specific piece of nucleic acid.

As used herein, the term "germline sequence" refers to a sequence of unrearranged immunoglobulin DNA sequences, including rodent (e.g. mouse) and human germline sequences. Any suitable source of unrearranged immunoglobulin DNA may be used. Human germline sequences may be obtained, for example, from JOINSOLVER® germline databases on the website for the National Institute of Arthritis and Musculoskeletal and Skin Diseases of the United States National Institutes of Health. Mouse germline sequences may be obtained, for example, as described in Giudicelli et al. (2005) *Nucleic Acids Res.* 33:D256-D261.

To examine the extent of inhibition of IL-23/IL-23R activity, for example, samples or assays comprising a given, e.g., protein, gene, cell, or organism, are treated with a potential activating or inhibiting agent and are compared to control samples without the agent. Control samples, i.e., not treated with agent, are assigned a relative activity value of 100% Inhibition is achieved when the activity value relative to the control is about 90% or less, typically 85% or less, more typically 80% or less, most typically 75% or less, generally 70% or less, more generally 65% or less, most generally 60% or less, typically 55% or less, usually 50% or less, more usually 45% or less, most usually 40% or less, preferably 35% or less, more preferably 30% or less, still more preferably 25% or less, and most preferably less than 20%. Activation is achieved when the activity value relative to the control is about 110%, generally at least 120%, more generally at least 140%, more generally at least 160%, often at least 180%, more often at least 2-fold, most often at least 2.5-fold, usually at least 5-fold, more usually at least 10-fold, preferably at least 20-fold, more preferably at least 40-fold, and most preferably over 40-fold higher.

Endpoints in activation or inhibition can be monitored as follows. Activation, inhibition, and response to treatment, e.g., of a cell, physiological fluid, tissue, organ, and animal or human subject, can be monitored by an endpoint. The endpoint may comprise a predetermined quantity or percentage of, e.g., an indicia of inflammation, oncogenicity, or cell degranulation or secretion, such as the release of a cytokine, toxic oxygen, or a protease. The endpoint may comprise, e.g., a predetermined quantity of ion flux or transport; cell migration; cell adhesion; cell proliferation; potential for metastasis; cell differentiation; and change in phenotype, e.g., change in expression of gene relating to inflammation, apoptosis, transformation, cell cycle, or metastasis (see, e.g., Knight (2000) *Ann. Clin. Lab. Sci.* 30:145-158; Hood and Cheresh (2002) *Nature Rev. Cancer* 2:91-100; Timme et al. (2003) *Curr. Drug Targets* 4:251-261; Robbins and Itzkowitz (2002) *Med. Clin. North Am.* 86:1467-1495; Grady and Markowitz (2002) *Annu. Rev. Genomics Hum. Genet.* 3:101-128; Bauer, et al. (2001) *Glia* 36:235-243; Stanimirovic and Satoh (2000) *Brain Pathol.* 10:113-126).

An endpoint of inhibition is generally 75% of the control or less, preferably 50% of the control or less, more preferably 25% of the control or less, and most preferably 10% of the control or less. Generally, an endpoint of activation is at least 150% the control, preferably at least two times the control, more preferably at least four times the control, and most preferably at least 10 times the control.

"Small molecule" is defined as a molecule with a molecular weight that is less than 10 kDa, typically less than 2 kDa, and preferably less than 1 kDa. Small molecules include, but are not limited to, inorganic molecules, organic molecules, organic molecules containing an inorganic component, molecules comprising a radioactive atom, synthetic molecules, peptide mimetics, and antibody mimetics. As a therapeutic, a small molecule may be more permeable to cells, less susceptible to degradation, and less apt to elicit an immune response than large molecules. Small molecules, such as peptide mimetics of antibodies and cytokines, as well as small molecule toxins are described. See, e.g., Casset et al. (2003) *Biochem. Biophys. Res. Commun.* 307:198-205; Muyldermans (2001) *J. Biotechnol.* 74:277-302; Li (2000) *Nat. Biotechnol.* 18:1251-1256; Apostolopoulos et al. (2002) *Curr. Med. Chem.* 9:411-420; Monfardini et al. (2002) *Curr. Pharm. Des.* 8:2185-2199; Domingues et al. (1999) *Nat. Struct. Biol.* 6:652-656; Sato and Sone (2003) *Biochem. J.* 371:603-608; U.S. Pat. No. 6,326,482.

"Specifically" or "selectively" binds, when referring to a ligand/receptor, antibody/antigen, or other binding pair, indicates a binding reaction that is determinative of the presence of the protein in a heterogeneous population of proteins and other biologics. Thus, under designated conditions, a specified ligand binds to a particular receptor and does not bind in a significant amount to other proteins present in the sample. As used herein, an antibody is said to bind specifically to a polypeptide comprising a given sequence (in this case IL-23R) if it binds to polypeptides comprising the sequence of IL-23R but does not bind to proteins lacking the sequence of IL-23R. For example, an antibody that specifically binds to a polypeptide comprising IL-23R may bind to a FLAG®-tagged form of IL-23R but will not bind to other FLAG®-tagged proteins.

The antibody, or binding composition derived from the antigen-binding site of an antibody, of the contemplated method binds to its antigen with an affinity that is at least two fold greater, preferably at least ten times greater, more preferably at least 20-times greater, and most preferably at least 100-times greater than the affinity with unrelated antigens. In a preferred embodiment the antibody will have an affinity that is greater than about $10^9$ liters/mol, as determined, e.g., by Scatchard analysis. Munsen et al. (1980) *Analyt. Biochem.* 107:220-239.

As used herein, the term "immunomodulatory agent" refers to natural or synthetic agents that suppress or modulate an immune response. The immune response can be a humoral or cellular response. Immunomodulatory agents encompass immunosuppressive or anti-inflammatory agents.

"Immunosuppressive agents," "immunosuppressive drugs," or "immunosuppressants" as used herein are therapeutics that are used in immunosuppressive therapy to inhibit or prevent activity of the immune system. Clinically they are used to prevent the rejection of transplanted organs and tissues (e.g. bone marrow, heart, kidney, liver), and/or in the treatment of autoimmune diseases or diseases that are most likely of autoimmune origin (e.g. rheumatoid arthritis, myasthenia gravis, systemic lupus erythematosus, ulcerative colitis, multiple sclerosis). Immunosuppressive drugs can be classified into four groups: glucocorticoids cytostatics; antibodies (including Biological Response Modifiers or DMARDs); drugs acting on immunophilins; other drugs, including known chemotherapeutic agents used in the treatment of proliferative disorders. For multiple sclerosis, in particular, the antibodies of the present invention can be administered in conjunction with a new class of myelin binding protein-like therapeutics, known as copaxones.

"Anti-inflammatory agents" or "anti-inflammatory drugs", is used to represent both steroidal and non-steroidal therapeutics. Steroids, also known as corticosteroids, are drugs that closely resemble cortisol, a hormone produced naturally by adrenal glands. Steroids are used as the main treatment for certain inflammatory conditions, such as: Systemic vasculitis (inflammation of blood vessels); and Myositis (inflammation of muscle). Steroids might also be used selectively to treat inflammatory conditions such as: rheumatoid arthritis (chronic inflammatory arthritis occurring in joints on both sides of the body); systemic lupus erythematosus (a generalized disease caused by abnormal immune system function); Sjögren's syndrome (chronic disorder that causes dry eyes and a dry mouth).

Non-steroidal anti-inflammatory drugs, usually abbreviated to NSAIDs, are drugs with analgesic, antipyretic and anti-inflammatory effects—they reduce pain, fever and inflammation. The term "non-steroidal" is used to distinguish these drugs from steroids, which (amongst a broad range of other effects) have a similar eicosanoid-depressing, anti-inflammatory action. NSAIDs are generally indicated for the symptomatic relief of the following conditions: rheumatoid arthritis; osteoarthritis; inflammatory arthropathies (e.g. ankylosing spondylitis, psoriatic arthritis, Reiter's syndrome); acute gout; dysmenorrhoea; metastatic bone pain; headache and migraine; postoperative pain; mild-to-moderate pain due to inflammation and tissue injury; pyrexia; and renal colic. NSAIDs include salicylates, arlyalknoic acids, 2-arylpropionic acids (profens), N-arylanthranilic acids (fenamic acids), oxicams, coxibs, and sulphonanilides.

II. General

The present invention provides engineered anti-IL-23R antibodies and uses thereof to treat inflammatory, autoimmune, and proliferative disorders.

A number of cytokines have a role in the pathology or repair of neurological disorders. IL-6, IL-17, interferon-gamma (IFNgamma, IFN-γ), and granulocyte colony-stimulating factor (GM-CSF) have been associated with multiple sclerosis. Matusevicius et al. (1999) *Multiple Sclerosis* 5:101-104; Lock et al. (2002) *Nature Med.* 8:500-508. IL-1alpha, IL-1beta, and transforming growth factor-beta 1 (TGF-beta1) play a role in ALS, Parkinson's disease, and Alzheimer's disease. Hoozemans et al. (2001) *Exp. Gerontol.* 36:559-570; Griffin and Mrak (2002) *J. Leukocyte Biol.* 72:233-238; Ilzecka et al. (2002) *Cytokine* 20:239-243. TNF-alpha, IL-1beta, IL-6, IL-8, interferon-gamma, and IL-17 appear to modulate response to brain ischemia. See, e.g., Kostulas et al. (1999) *Stroke* 30:2174-2179; Li et al. (2001) *J. Neuroimmunol.* 116:5-14. Vascular endothelial cell growth factor (VEGF) is associated with ALS. Cleveland and Rothstein (2001) *Nature* 2:806-819.

Inflammatory bowel disorders, e.g., Crohn's disease, ulcerative colitis, celiac disease, and irritable bowel syndrome, are mediated by cells of the immune system and by cytokines For example, Crohn's disease is associated with increased IL-12 and IFNγ, while ulcerative colitis is associated with increased IL-5, IL-13, and transforming growth factor-beta (TGFbeta). IL-17 expression may also increase in Crohn's disease and ulcerative colitis. See, e.g., Podolsky (2002) *New Engl. J. Med.* 347:417-429; Bouma and Strober (2003) *Nat. Rev. Immunol.* 3:521-533; Bhan et al. (1999) *Immunol. Rev.* 169:195-207; Hanauer (1996) *New Engl. J. Med.* 334:841-848; Green (2003) *The Lancet* 362:383-391; McManus (2003) *New Engl. J. Med.* 348:2573-2574; Horwitz and Fisher (2001) *New Engl. J. Med.* 344:1846-1850; Andoh et al. (2002) *Int. J. Mol. Med.* 10:631-634; Nielsen et al. (2003) *Scand. J. Gastroenterol.* 38:180-185; Fujino et al. (2003) *Gut* 52:65-70.

IL-23 receptor is a heterodimeric complex of IL-23R and IL-12Rβ1 subunits. See Parham et al. (2000) *J. Immunol.* 168:5699. IL-12 receptor is a complex of IL-12Rβ1 and IL-12Rβ2 subunits. See Presky et al. (1996) *Proc. Nat'l Acad. Sci. USA* 93:14002. IL-23R has been implicated as a critical genetic factor in the inflammatory bowel disorders Crohn's disease and ulcerative colitis. Duerr et al. (2006) *Science* 314:1461. A genome-wide association study found that the gene for IL-23R was highly associated with Crohn's disease, with an uncommon coding variant (Arg381Gln) conferring strong protection against the disease. This genetic association confirms prior biological findings (Yen et al. (2006) *J. Clin. Investigation* 116:1218) suggesting that IL-23 and its receptor (including IL-23R) are promising targets for new therapeutic approached to treating IBD.

Inflammatory diseases of the skin, joints, CNS, as well as proliferative disorders elicit similar immune responses, thus IL-23/IL-23R blockade should provide inhibition of these immune mediated inflammatory disorders, without comprising the host ability to fight systemic infections. Antagonizing IL-23/IL-23R should relieve the inflammation associated with inflammatory bowel disease, Crohn's disease, ulcerative colitis, rheumatoid arthritis, psoriatic arthritis, psoriasis, ankylosing spondylitis and atopic dermatitis. Use of IL-23/IL-23R inhibitors will also provide inhibition of proliferative disorders, e.g., cancer and autoimmune disorders e.g., multiple sclerosis, type I diabetes, and SLE. Descriptions of IL-23 in these various disorders can be found in the following published PCT applications: WO 04/081190; WO 04/071517; WO 00/53631; and WO 01/18051. IL-23/IL-23R inhibitors may also find use in treatment of infections, including chronic infections, such as bacterial, mycobacterial, viral and fungal infections.

The p19 subunit of IL-23 is a member of the IL-6 family of helical cytokines The p19 subunit interacts with three cytokine receptor subunits to form the competent signaling complex. When expressed in a cell, the p19 subunit first forms a complex with the p40 subunit, which it shares with IL-12. As noted above, the p19p40 complex is secreted from the cell as a heterodimeric protein and is called IL-23 (see, e.g., Oppmann et al., supra).

The cellular receptor complex required to transduce the IL-23 signal consists of two members of the tall signaling receptor subunits of the IL-6/IL-12 family of cytokines, the IL-23-specific IL-23R (see, e.g., Parham et al. supra) and the IL-12Rβ1 subunit, which is shared with IL-12. The amino acid sequence for human IL-23R is found at GenBank Accession No: AAM44229 (SEQ ID NO: 41), and an mRNA sequence is found at GenBank Accession No: NM_144701. The human IL-23R gene is described at NCBI GeneID No. 149233. The amino acid sequence for mouse (*mus musculus*) IL-23R is found at GenBank Accession No: AAM44230, and provided at SEQ ID NO: 42. Amino acid residues 1-23 of both human and mouse IL-23R sequences represent signal sequences that are not present in the mature forms of IL-23R. The amino acid sequences for human and mouse (*mus musculus*) IL-12Rβ1 are found at GenBank Accession Nos: NP_005526 and Q60837, and provided at SEQ ID NOs: 43 and 44, respectively. Amino acid residues 1-24 and 1-19 represent signal sequences for human and mouse IL-12Rβ1, respectively.

Comparison of the natural roles of IL-12 and IL-23 suggest that targeting IL-23 for inhibition will cause fewer adverse side-effects when compared with inhibition of IL-12, or inhibition of both IL-23 and IL-12. Bowman et al. (2006) *Curr. Opin. Infect. Dis.* 19:245. While IL-12 is critical to mounting a systemic Th1-mediated immune responses, IL-23 (along with IL-6 and TNF-α) is thought to be responsible for promotion and maintenance of Th-17 cells. Such Th-17 cells are believed to be involved in responses to catastrophic injury, such as breach of the mucosal barrier of the lung or gut, and the resulting exposure to the deadly pathogens *K. pneumoniae* and *C. rodentium*. Such catastrophic injuries would almost certainly require an immediate immune response in the form of massive neutrophil influx. See Cua and Kastelein (2006) *Nature Immunology* 7:557. Because such catastrophic injuries and infections are relatively rare in modern society, and can be treated with antibiotics if they do occur, this Th-17 "nuclear option" may not be as critical to survival as it was earlier in human evolution. This suggests that disruption of IL-23/IL-23 receptor signaling may have a relatively minor side effect profile, since its natural activity is of little importance in modern society. See McKenzie et al. (2006) *Trends Immunol.* 27:17.

The distinct subunit compositions of IL-12 receptor and IL-23 receptor make it possible to design therapy that targets only IL-23 receptor but not IL-12 receptor. Compounds that bind to and inhibit the activity of IL-23p19 or IL-23R, either in isolation of as components of their respective heterodimeric complexes, will inhibit IL-23 but not IL-12. There may also be compounds that are capable of binding to IL-12p40 when present in IL-23 but not in IL-12, or compounds that bind to and inhibit IL-12Rβ1 when present in the IL-23 receptor but not in IL-12 receptor. Such specific binding agents will also inhibit IL-23 activity but not IL-12 activity. IL-23/IL-23R specific agents would be expected to be safer (i.e. have a lower side effect profile) than agents that also inhibit IL-12.

Much of the early work on inhibition of IL-12 involved inhibition of IL-12p40. It has been subsequently realized that these experiments involved not only inhibition of IL-12 but also inhibition of IL-23, and that in fact the effects in many of these experiments were the result of inhibition of IL-23. Many disorders once thought to be caused by a pathogenic Th1 response, which could be ameliorated by inhibition of IL-12, have been shown instead to be caused by a Th17 response, which is ameliorated by inhibition of IL-23. Yen et al. (2006) *J. Clin. Invest.* 116:1310; Iwakura and Ishingame (2006) *J. Clin. Invest.* 116:1218.

IL-23 receptor, and specifically IL-23R, represents an attractive target for therapeutic intervention. IL-23R is expressed on the surface of $T_H17$ cells, and the antibodies of the present invention may be used to deliver a cytotoxic payload specifically to that T-cell subset. Such cell-specific immunotherapy is particularly suited to treatment of disorders in which $T_H17$ cells migrate from a tissue in which they are induced (e.g. the gut, lung or skin) into another tissue, such as CNS, since the cells could be targeted and killed prior to infiltrating the new target tissue and inducing disease (e.g. MS in the CNS). See Chen et al. (2006) *J. Clin. Invest.* 116:1317.

In other embodiments, however, it may be preferable to avoid cytotoxic effects in cells expressing IL-23R, but instead to simply block IL-23 signaling. In the case of treatment of tumors (see, e.g., WO 2004/081190), for example, it may be preferable to block IL-23 signaling in Th0 cells, and thus block Th17 formation, without inducing cell killing. The Th0 cells will then be available for production cells of the Th1 lineage, induced by IL-12, which can then engage in productive immune surveillance of the tumor cells with beneficial effect. The compositions and methods of the present invention encompass both scenarios by providing binding compounds (antibodies) that may or may not enhance killing of IL-23R expressing cells, depending on which is the preferred approach for the specific therapeutic use. In some embodiments, antibodies or fragments thereof lacking effector function may be used, such as IgG antibodies other than subclass IgG$_1$, or Fab or other antibody fragments.

Targeting IL-23R has advantages over targeting IL-12Rβ1, the other subunit of the heterodimeric IL-23 receptor, since inhibition of IL-23R will disrupt IL-23 signaling but not disrupt IL-12 signaling Inhibition of IL-12Rβ1 would disrupt signaling of both IL-23 and IL-12. In general principle a more narrowly targeted therapy is preferable, and in this specific case there are good reasons to expect that disruption of IL-12 would reduce the subject's ability to resist some infectious diseases and to maintain tumor surveillance.

Targeting IL-23R has advantages over targeting IL-23p19 despite the fact that the two therapeutic approaches both act by disrupting IL-23 signaling through its receptor. IL-23R is present at significantly lower levels than IL-23p19, and the amount of anti-IL-23R antibody necessary to block IL-23R would be expected to be correspondingly lower than would be required to block the activity of p19 in a subject. This reduction in the amount of antibody may provide several advantages, such as reducing the expense of treatment, decreasing the concentration and/or volume of the drug to be delivered, and facilitating less frequent administration. In addition, targeting of IL-23p 19 may alter the circulating level of IL-12p40, which is a subunit of both IL-23 and IL-12, and also appears to exist in a p40 homodimer form. Because the potential biological effects of alterations in the levels of IL-12 and/or IL-12p40 homodimer are not fully understood, it would be preferable to block IL-23 signaling in a way that doesn't involve targeting the soluble cytokine (IL-23), but instead targets the IL-23-specific receptor subunit IL-23R.

III. Generation of IL-23R Specific Antibodies

Any suitable method for generating monoclonal antibodies may be used. For example, a recipient may be immunized with IL-23R or a fragment thereof. Any suitable method of immunization can be used. Such methods can include adjuvants, other immunostimulants, repeated booster immunizations, and the use of one or more immunization routes. Any suitable source of IL-23R can be used as the immunogen for the generation of the non-human antibody of the compositions and methods disclosed herein. Such forms include, but are not limited whole protein, peptide(s), and epitopes generated through recombinant, synthetic, chemical or enzymatic degradation means known in the art. In preferred embodiments the immunogen comprises the extracellular portion of IL-23R. The domain structure of IL-23R is discussed in U.S. Pat. No. 6,756,481, in which the extracellular domain is predicted to comprise amino acids 1-328 of the mature form of human IL-23R, corresponding to residues 24-351 of SEQ ID NO: 41 of the present application. See also WO 2004/052157. The extracellular domain may be defined differently depending on the proposed purpose, such as design of an immunogenic polypeptide construct.

Any form of the antigen can be used to generate the antibody that is sufficient to generate a biologically active antibody. Thus, the eliciting antigen may be a single epitope, multiple epitopes, or the entire protein alone or in combination with one or more immunogenicity enhancing agents known in the art. The eliciting antigen may be an isolated full-length protein, a cell surface protein (e.g., immunizing with cells transfected with at least a portion of the antigen), or a soluble protein (e.g., immunizing with only the extracellular domain portion of the protein). The antigen may be produced in a genetically modified cell. The DNA encoding the antigen may genomic or non-genomic (e.g., cDNA) and encodes at least a portion of the extracellular domain. As used herein, the term "portion" refers to the minimal number of amino acids or nucleic acids, as appropriate, to constitute an immunogenic epitope of the antigen of interest. Any genetic vectors suitable for transformation of the cells of interest may be employed, including but not limited to adenoviral vectors, plasmids, and non-viral vectors, such as cationic lipids.

Any suitable method can be used to elicit an antibody with the desired biologic properties to inhibit IL-23/IL-23R. It is desirable to prepare monoclonal antibodies (mAbs) from various mammalian hosts, such as mice, rats, other rodents, humans, other primates, etc. Description of techniques for preparing such monoclonal antibodies may be found in, e.g., Stites et al. (eds.) BASIC AND CLINICAL IMMUNOLOGY (4th ed.) Lange Medical Publications, Los Altos, Calif., and references cited therein; Harlow and Lane (1988) ANTIBODIES: A LABORATORY MANUAL CSH Press; Goding (1986) MONOCLONAL ANTIBODIES: PRINCIPLES AND PRACTICE (2d ed.) Academic Press, New York, N.Y. Thus, monoclonal antibodies may be obtained by a variety of techniques familiar to researchers skilled in the art. Typically, spleen cells from an animal immunized with a desired antigen are immortalized, commonly by fusion with a myeloma cell. See Kohler and Milstein (1976) Eur. J. Immunol. 6:511-519. Alternative methods of immortalization include transformation with Epstein Barr Virus, oncogenes, or retroviruses, or other methods known in the art. See, e.g., Doyle et al. (eds. 1994 and periodic supplements) CELL AND TISSUE CULTURE: LABORATORY PROCEDURES, John Wiley and Sons, New York, N.Y. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences that encode a monoclonal antibody or a antigen binding fragment thereof by screening a DNA library from human B cells according, e.g., to the general protocol outlined by Huse et al. (1989) Science 246:1275-1281.

Other suitable techniques involve selection of libraries of antibodies in phage or similar vectors. See, e.g., Huse et al. supra; and Ward et al. (1989) Nature 341:544-546. The polypeptides and antibodies of the present invention may be used with or without modification, including chimeric or humanized antibodies. Frequently, the polypeptides and antibodies will be labeled by joining, either covalently or non-covalently, a substance that provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced, see Cabilly U.S. Pat. No. 4,816,567; and Queen et al. (1989) Proc. Nat'l Acad. Sci. USA 86:10029-10033; or made in transgenic mice, see Mendez et al. (1997) Nature Genetics 15:146-156. See also Abgenix and Medarex technologies.

Antibodies or binding compositions against predetermined fragments of IL-23R can be raised by immunization of animals with conjugates of the polypeptide, fragments, peptides, or epitopes with carrier proteins. Monoclonal antibodies are prepared from cells secreting the desired antibody. These antibodies can be screened for binding to normal or defective IL-23R. These monoclonal antibodies will usually bind with at least a $K_d$ of about 1 µM, more usually at least about 300 nM, 30 nM, 10 nM, 3 nM, 1 nM, 300 pM, 100 pM, 30 pM, 10 pM, 1 pM or better, usually determined by ELISA or BIAcore® label-free interaction analysis system. Suitable non-human antibodies may also be identified using the biologic assays described in Examples 5, 6 and 7, below.

Hybridomas expressing antibodies 8B10 (rat IgG2a kappa) and 20D7 (mouse IgG1 kappa) were deposited pursuant to the Budapest Treaty with American Type Culture Collection (ATCC-Manassas, Va. USA) on Aug. 17, 2006 under Accession Numbers PTA-7800 and PTA-7801, respectively. All restrictions imposed by the depositor on the availability to the public of the deposited material will be irrevocably removed upon granting of a patent.

IV. Humanization of IL-23R Specific Antibodies

Any suitable non-human antibody can be used as a source for the hypervariable region. Sources for non-human antibodies include, but are not limited to, murine (e.g. *Mus musculus*), rat (e.g. *Rattus norvegicus*), Lagomorphs (including rabbits), bovine, and primates. For the most part, humanized antibodies are human immunoglobulins (recipient antibody) in which hypervariable region residues of the recipient are replaced by hypervariable region residues from a non-human species (donor antibody) such as mouse, rat, rabbit or non-human primate having the desired specificity, affinity, and capacity. In some instances, Fv framework region (FR) residues of the human immunoglobulin are replaced by corresponding non-human residues. Furthermore, humanized antibodies may comprise residues that are not found in the recipient antibody or in the donor antibody. These modifications are made to further refine antibody performance of the desired biological activity. For further details, see Jones et al. (1986) Nature 321:522-525; Reichmann et al. (1988) Nature 332:323-329; and Presta (1992) Curr. Op. Struct. Biol. 2:593-596.

Methods for recombinantly engineering antibodies have been described, e.g., by Boss et al. (U.S. Pat. No. 4,816,397), Cabilly et al. (U.S. Pat. No. 4,816,567), Law et al. (European Patent Application Publication No. EP438310A1) and Winter (European Patent Application Publication No. EP239400B1).

Amino acid sequence variants of humanized anti-IL-23R antibody are prepared by introducing appropriate nucleotide changes into the humanized anti-IL-23R antibody DNA, or by peptide synthesis. Such variants include, for example, deletions from, and/or insertions into, and/or substitutions of, residues within the amino acid sequences shown for the humanized anti-IL-23R antibody. Any combination of deletion, insertion, and substitution is made to arrive at the final construct, provided that the final construct possesses the desired characteristics. The amino acid changes also may alter post-translational processes of the humanized anti-IL-23R antibody, such as changing the number or position of glycosylation sites.

A useful method for identification of certain residues or regions of the humanized anti-IL-23R antibody polypeptide that are preferred locations for mutagenesis is called "alanine scanning mutagenesis," as described by Cunningham and Wells (1989) *Science* 244: 1081-1085. Here, a residue or group of target residues are identified (e.g., charged residues such as Arg, Asp, His, Lys, and Glu) and replaced by a neutral or negatively charged amino acid (most preferably alanine or polyalanine) to affect the interaction of the amino acids with IL-23R antigen. The amino acid residues demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, Ala scanning or random mutagenesis is conducted at the target codon or region and the expressed humanized anti-IL-23R antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include humanized anti-IL-23R antibody with an N-terminal methionyl residue or the antibody fused to an epitope tag. Other insertional variants of the humanized anti-IL-23R antibody molecule include the fusion to the N- or C-terminus of humanized anti-IL-23R antibody of an enzyme or a polypeptide that increases the serum half-life of the antibody.

Another type of variant is an amino acid substitution variant. These variants have at least one amino acid residue in the humanized anti-IL-23R antibody molecule removed and a different residue inserted in its place. The sites of greatest interest for substitutional mutagenesis include the hypervariable loops, but FR alterations are also contemplated.

Another type of amino acid variant of the antibody alters the original glycosylation pattern of the antibody. By altering is meant deleting one or more carbohydrate moieties found in the antibody, and/or adding one or more glycosylation sites that are not present in the antibody. Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Yet another type of amino acid variant is the substitution of residues to provide for greater chemical stability of the final humanized antibody. For example, an asparagine (N) residue may be changed to reduce the potential for formation of isoaspartate at any NG sequences within a rodent CDR. A similar problem may occur at a DG sequence. Reissner and Aswad (2003) *Cell. Mol. Life Sci.* 60:1281. Isoaspartate formation may debilitate or completely abrogate binding of an antibody to its target antigen. Presta (2005) *J. Allergy Clin. Immunol.* 116:731 at 734. In one embodiment, the asparagine is changed to glutamine (Q). It may also be desirable to alter an amino acid adjacent to an asparagine (N) or glutamine (Q) residue to reduce the likelihood of deamidation, which occurs at greater rates when small amino acids occur adjacent to asparagine or glutamine. Bischoff & Kolbe (1994) *J. Chromatog.* 662:261. In addition, methionine residues in rodent CDRs may be changed to reduce the possibility that the methionine sulfur would oxidize, which could reduce antigen binding affinity and also contribute to molecular heterogeneity in the final antibody preparation. Id. In one embodiment, the methionine is changed to alanine (A). Antibodies with such substitutions are subsequently screened to ensure that the substitutions do not decrease IL-23R binding affinity to unacceptable levels.

Nucleic acid molecules encoding amino acid sequence variants of humanized IL-23R specific antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of humanized anti-IL-23R antibody.

Ordinarily, amino acid sequence variants of the humanized anti-IL-23R antibody will have an amino acid sequence having at least 75% amino acid sequence identity with the original humanized antibody amino acid sequences of either the heavy or the light chain more preferably at least 80%, more preferably at least 85%, more preferably at least 90%, and most preferably at least 95%, 98% or 99%. Identity or homology with respect to this sequence is defined herein as the percentage of amino acid residues in the candidate sequence that are identical with the humanized anti-IL-23R residues, after aligning the sequences and introducing gaps, if necessary, to achieve the maximum percent sequence identity, and not considering any conservative substitutions as part of the sequence identity. None of N-terminal, C-terminal, or internal extensions, deletions, or insertions into the antibody sequence shall be construed as affecting sequence identity or homology.

The humanized antibody can be selected from any class of immunoglobulins, including IgM, IgG, IgD, IgA, and IgE. Preferably, the antibody is an IgG antibody. Any isotype of IgG can be used, including $IgG_1$, $IgG_2$, $IgG_3$, and $IgG_4$. Variants of the IgG isotypes are also contemplated. The humanized antibody may comprise sequences from more than one class or isotype. Optimization of the necessary constant domain sequences to generate the desired biologic activity is readily achieved by screening the antibodies in the biological assays described in the Examples.

Likewise, either class of light chain can be used in the compositions and methods herein. Specifically, kappa, lambda, or variants thereof are useful in the present compositions and methods.

Any suitable portion of the CDR sequences from the non-human antibody can be used. The CDR sequences can be mutagenized by substitution, insertion or deletion of at least one residue such that the CDR sequence is distinct from the human and non-human antibody sequence employed. It is contemplated that such mutations would be minimal. Typically, at least 75% of the humanized antibody residues will correspond to those of the non-human CDR residues, more often 90%, and most preferably greater than 95%.

Any suitable portion of the FR sequences from the human antibody can be used. The FR sequences can be mutagenized by substitution, insertion or deletion of at least one residue such that the FR sequence is distinct from the human and non-human antibody sequence employed. It is contemplated that such mutations would be minimal. Typically, at least 75% of the humanized antibody residues will correspond to those of the human FR residues, more often 90%, and most preferably greater than 95%, 98% or 99%.

CDR and FR residues are determined according to the standard sequence definition of Kabat. Kabat et al. (1987) Sequences of Proteins of Immunological Interest, National Institutes of Health, Bethesda Md. SEQ ID NOs: 1-5 show the heavy chain variable domain sequences of various mouse and rat anti-human IL-23R antibodies, and SEQ ID NOs: 6-10 depict the light chain variable domain sequences. SEQ ID NOs: 45-47 show the heavy chain variable domain sequences of various forms of humanized mouse anti-human IL-23R clone 20D7 antibody, and SEQ ID NOs: 48-49 and 53 depict the light chain variable domain sequences. FIGS. 1 and 2 provide sequence lineups of heavy and light chain variable domains of the various antibodies of the present invention. CDRs are indicated in the figures, and the individual CDR sequences are each presented with unique Sequence Identifiers (SEQ ID NOs: 11-40), as indicated in Tables 2 and 4.

TABLE 2

Light Chain Sequences and Domains

| ANTIBODY CLONE | SEQ ID NO: | $V_L$ RESIDUES | LIGHT CHAIN CDR RESIDUES | | |
|---|---|---|---|---|---|
| | | | CDR-L1 | CDR-L2 | CDR-L3 |
| 41F11 | 6 | 1-108 | 24-34 | 50-56 | 89-97 |
| 8B10 | 7 | 1-108 | 24-34 | 50-56 | 89-97 |
| 3C11 | 8 | 1-108 | 24-34 | 50-56 | 89-97 |
| 20D7 | 9 | 1-114 | 24-40 | 56-62 | 95-103 |
| 20E5 | 10 | 1-103 | 24-34 | 50-56 | 89-97 |
| hu20D7-IV | 48 | 1-115 | 24-40 | 56-62 | 95-103 |
| hu20D7-II-a | 49 | 1-115 | 24-40 | 56-62 | 95-103 |
| hu20D7-II-b | 53 | 1-115 | 24-40 | 56-62 | 95-103 |

TABLE 3

Heavy Chain Sequences and Domains

| ANTIBODY CLONE | SEQ ID NO: | $V_H$ RESIDUES | HEAVY CHAIN CDR RESIDUES | | |
|---|---|---|---|---|---|
| | | | CDR-H1 | CDR-H2 | CDR-H3 |
| 41F11 | 1 | 1-117 | 26-35 | 50-66 | 99-106 |
| 8B10 | 2 | 1-119 | 26-35 | 50-68 | 101-108 |
| 3C11 | 3 | 1-128 | 26-37 | 52-67 | 100-117 |
| 20D7 | 4 | 1-120 | 26-35 | 50-66 | 99-109 |
| 20E5 | 5 | 1-119 | 26-35 | 50-66 | 99-108 |
| hu20D7-a | 45 | 1-120 | 26-35 | 50-66 | 99-109 |
| hu20D7-b | 46 | 1-120 | 26-35 | 50-66 | 99-109 |
| hu20D7-c | 47 | 1-120 | 26-35 | 50-66 | 99-109 |

In one embodiment, CDRs include variants of any single sequence CDR disclosed herein (SEQ ID NOs: 11-40 and 52), in which the variant comprises 1, 2, 3, 4, 5, 6, 7, 8, 9, 10 or more conservative amino acid substitutions relative to the disclosed sequence, as determined using Table 1.

Also contemplated are chimeric antibodies. As noted above, typical chimeric antibodies comprise a portion of the heavy and/or light chain identical with, or homologous to, corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity. See U.S. Pat. No. 4,816,567; and Morrison et al. (1984) *Proc. Natl. Acad. Sci. USA* 81: 6851-6855.

Bispecific antibodies are also useful in the present methods and compositions. As used herein, the term "bispecific antibody" refers to an antibody, typically a monoclonal antibody, having binding specificities for at least two different antigenic epitopes. In one embodiment, the epitopes are from the same antigen. In another embodiment, the epitopes are from two different antigens. Methods for making bispecific antibodies are known in the art. For example, bispecific antibodies can be produced recombinantly using the co-expression of two immunoglobulin heavy chain/light chain pairs. See, e.g., Milstein et al. (1983) Nature 305: 537-39. Alternatively, bispecific antibodies can be prepared using chemical linkage. See, e.g., Brennan et al. (1985) *Science* 229:81. Bispecific antibodies include bispecific antibody fragments. See, e.g., Holliger et al. (1993) *Proc. Natl. Acad. Sci. U.S.A.* 90:6444-48, Gruber et al. (1994) *J. Immunol.* 152:5368.

In yet other embodiments, different constant domains may be appended to humanized $V_L$ and $V_H$ regions derived from the CDRs provided herein. For example, if a particular intended use of an antibody (or fragment) of the present invention were to call for altered effector functions, a heavy chain constant domain other than IgG1 may be used. Although IgG1 antibodies provide for long half-life and for effector functions, such as complement activation and antibody-dependent cellular cytotoxicity, such activities may not be desirable for all uses of the antibody. In such instances an IgG4 constant domain, for example, may be used.

V. Biological Activity of Humanized Anti-IL-23R Antibodies

Antibodies having the characteristics identified herein as being desirable in a humanized anti-IL-23R antibody can be screened for inhibitory biologic activity in vitro or suitable binding affinity. Antagonist antibodies may be distinguished from agonist antibodies using the biological assays provided at Examples 5, 6 and 7. Antibodies that exhibit agonist activity will not block the activity of IL-23, but will instead stimulate the response typically caused by IL-23, such as increasing cell proliferation in the Ba/F3 assay of Example 5 and/or increasing IL-17 production in the splenocyte assay of Example 6. Although agonist antibodies may find use in some therapeutic indications, the anti-IL-23R antibodies disclosed herein are intended to be antagonist antibodies unless otherwise indicated.

To screen for antibodies that bind to the epitope on human IL-23R bound by an antibody of interest (e.g., those that block binding of IL-23), a routine cross-blocking assay such as that described in ANTIBODIES, A LABORATORY MANUAL, Cold Spring Harbor Laboratory, Ed Harlow and David Lane (1988), can be performed. Antibodies that bind to the same epitope are likely to cross-block in such assays, but not all cross-blocking antibodies will necessarily bind at precisely the same epitope since cross-blocking may result from steric hindrance of antibody binding by antibodies bind at overlapping epitopes, or even nearby non-overlapping epitopes.

Alternatively, epitope mapping, e.g., as described in Champe et al. (1995) *J. Biol. Chem.* 270:1388-1394, can be performed to determine whether the antibody binds an epitope of interest. "Alanine scanning mutagenesis," as described by Cunningham and Wells (1989) *Science* 244: 1081-1085, or some other form of point mutagenesis of amino acid residues in human IL-23R may also be used to determine the functional epitope for an anti-IL-23R antibody of the present invention. Mutagenesis studies, however, may also reveal amino acid residues that are crucial to the overall three-dimensional structure of IL-23R but that are not directly involved in antibody-antigen contacts, and thus other methods may be necessary to confirm a functional epitope determined using this method.

The epitope bound by a specific antibody may also be determined by assessing binding of the antibody to peptides comprising fragments of human IL-23R (SEQ ID NO: 41). A series of overlapping peptides encompassing the sequence of IL-23R may be synthesized and screened for binding, e.g. in a direct ELISA, a competitive ELISA (where the peptide is assessed for its ability to prevent binding of an antibody to IL-23R bound to a well of a microtiter plate), or on a chip. Such peptide screening methods may not be capable of detecting some discontinuous functional epitopes, i.e. functional epitopes that involve amino acid residues that are not contiguous along the primary sequence of the IL-23R polypeptide chain.

The epitope bound by antibodies of the present invention may also be determined by structural methods, such as X-ray crystal structure determination (e.g., WO2005/044853), molecular modeling and nuclear magnetic resonance (NMR) spectroscopy, including NMR determination of the H-D exchange rates of labile amide hydrogens in IL-23R when free and when bound in a complex with an antibody of interest (Zinn-Justin et al. (1992) *Biochemistry* 31:11335-11347; Zinn-Justin et al. (1993) *Biochemistry* 32:6884-6891).

With regard to X-ray crystallography, crystallization may be accomplished using any of the known methods in the art (e.g. Giege et al. (1994) *Acta Crystallogr. D*50:339-350; McPherson (1990) *Eur. J. Biochem.* 189:1-23), including microbatch (e.g. Chayen (1997) *Structure* 5:1269-1274), hanging-drop vapor diffusion (e.g. McPherson (1976) *J. Biol. Chem.* 251:6300-6303), seeding and dialysis. It is desirable to use a protein preparation having a concentration of at least about 1 mg/mL and preferably about 10 mg/mL to about 20 mg/mL. Crystallization may be best achieved in a precipitant solution containing polyethylene glycol 1000-20,000 (PEG; average molecular weight ranging from about 1000 to about 20,000 Da), preferably about 5000 to about 7000 Da, more preferably about 6000 Da, with concentrations ranging from about 10% to about 30% (w/v). It may also be desirable to include a protein stabilizing agent, e.g. glycerol at a concentration ranging from about 0.5% to about 20%. A suitable salt, such as sodium chloride, lithium chloride or sodium citrate may also be desirable in the precipitant solution, preferably in a concentration ranging from about 1 mM to about 1000 mM. The precipitant is preferably buffered to a pH of from about 4.0 to about 10.0, preferably about 7.0 to 8.5, e.g. 8.0. Specific buffers useful in the precipitant solution may vary and are well-known in the art. Scopes, *Protein Purification: Principles and Practice*, Third ed., (1994) Springer-Verlag, New York. Examples of useful buffers include, but are not limited to, HEPES, Tris, MES and acetate. Crystals may be grow at a wide range of temperatures, including 2° C., 4° C., 8° C. and 26° C.

Antibody:antigen crystals may be studied using well-known X-ray diffraction techniques and may be refined using computer software such as X-PLOR (Yale University, 1992, distributed by Molecular Simulations, Inc.; see e.g. Blundell & Johnson (1985) *Meth. Enzymol.* 114 & 115, H. W. Wyckoff et al. eds., Academic Press; U.S. Patent Application Publication No. 2004/0014194), and BUSTER (Bricogne (1993) *Acta Cryst.* D49:37-60; Bricogne (1997) *Meth. Enzymol.* 276A:361-423, Carter & Sweet, eds.; Roversi et al. (2000) *Acta Cryst.* D56:1313-1323).

Additional antibodies binding to the same epitope as an antibody of the present invention may be obtained, for example, by screening of antibodies raised against IL-23R for binding to the epitope, or by immunization of an animal with a peptide comprising a fragment of human IL-23R comprising the epitope sequence. Antibodies that bind to the same functional epitope might be expected to exhibit similar biological activities, such as blocking receptor binding, and such activities can be confirmed by functional assays of the antibodies.

Antibody affinities may be determined using standard analysis. Preferred humanized antibodies are those that bind human IL-23R with a $K_d$ value of no more than about $1 \times 10^{-7}$ M; preferably no more than about $1 \times 10^{-8}$ M; more preferably no more than about $1 \times 10^{-9}$ M; and most preferably no more than about $1 \times 10^{-10}$ M or even $1 \times 10^{-11}$ M.

The antibodies and fragments thereof useful in the present compositions and methods are biologically active antibodies and fragments. As used herein, the term "biologically active" refers to an antibody or antibody fragment that is capable of binding the desired the antigenic epitope and directly or indirectly exerting a biologic effect. Typically, these effects result from the failure of IL-23 to bind IL-23 receptor. As used herein, the term "specific" refers to the selective binding of the antibody to the target antigen epitope. Antibodies can be tested for specificity of binding by comparing binding to IL-23R to binding to irrelevant antigen or antigen mixture under a given set of conditions. If the antibody binds to IL-23R at least 10, and preferably 50 times more than to irrelevant antigen or antigen mixture then it is considered to be specific. An antibody that "specifically binds" to IL-23R does not bind to proteins that do not comprise the IL-23R-derived sequences, i.e. "specificity" as used herein relates to IL-23R specificity, and not any other sequences that may be present in the protein in question. For example, as used herein, an antibody that "specifically binds" to a polypeptide comprising IL-23R will typically bind to FLAG®-hIL-23R, which is a fusion protein comprising IL-23R and a FLAG® peptide tag, but it does not bind to the FLAG® peptide tag alone or when it is fused to a protein other than IL-23R.

IL-23R-specific binding compounds of the present invention, such as inhibitory IL-23R specific antibodies, can inhibit its biological activity in any manner, including but not limited to reducing production of IL-1β and TNF by peritoneal macrophages and IL-17 by $T_H17$ T cells. See Langrish et al. (2004) *Immunol. Rev.* 202:96-105. Anti-IL-23R antibodies will also be able to inhibit the gene expression of IL-17A, IL-17F, CCL7, CCL17, CCL20, CCL22, CCR1, and GM-CSF. See Langrish et al. (2005) *J. Exp. Med.* 201:233-240. IL-23R-specific binding compounds of the present invention, such as anti IL-23R antibodies, will also block the ability of IL-23 to enhance proliferation or survival of $T_H17$ cells. Cua and Kastelein (2006) *Nat. Immunol.* 7:557-559. The inhibitory activity of anti-IL-23R antibodies will be useful in the treatment of inflammatory, autoimmune, and proliferative disorders. Examples of such disorders are described in PCT patent application publications WO 04/081190; WO 04/071517; WO 00/53631; and WO 01/18051.

VI. Pharmaceutical Compositions

To prepare pharmaceutical or sterile compositions including IL-23R antibody, the cytokine analogue or mutein, antibody thereto, or nucleic acid thereof, is admixed with a pharmaceutically acceptable carrier or excipient. See, e.g., *Remington's Pharmaceutical Sciences* and *U.S. Pharmacopeia: National Formulary*, Mack Publishing Company, Easton, Pa. (1984).

Formulations of therapeutic and diagnostic agents may be prepared by mixing with physiologically acceptable carriers, excipients, or stabilizers in the form of, e.g., lyophilized powders, slurries, aqueous solutions or suspensions. See, e.g., Hardman et al. (2001) *Goodman and Gilman's The Pharmacological Basis of Therapeutics*, McGraw-Hill, New York, N.Y.; Gennaro (2000) *Remington: The Science and Practice of Pharmacy*, Lippincott, Williams, and Wilkins, New York, N.Y.; Avis et al. (eds.) (1993) *Pharmaceutical Dosage Forms: Parenteral Medications*, Marcel Dekker, NY; Lieberman, et al. (eds.) (1990) *Pharmaceutical Dosage Forms: Tablets*, Marcel Dekker, NY; Lieberman et al. (eds.) (1990) *Pharmaceutical Dosage Forms: Disperse Systems*, Marcel Dekker, NY; Weiner and Kotkoskie (2000) *Excipient Toxicity and Safety*, Marcel Dekker, Inc., New York, N.Y.

Toxicity and therapeutic efficacy of the antibody compositions, administered alone or in combination with an immunosuppressive agent, can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio of $LD_{50}$ to $ED_{50}$. Antibodies exhibiting high therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration.

The mode of administration is not particularly important. Suitable routes of administration may, for example, include oral, rectal, transmucosal, or intestinal administration; parenteral delivery, including intramuscular, intradermal, subcutaneous, intramedullary injections, as well as intrathecal, direct intraventricular, intravenous, intraperitoneal, intranasal, or intraocular injections. Administration of antibody used in the pharmaceutical composition or to practice the method of the present invention can be carried out in a variety of conventional ways, such as oral ingestion, inhalation, topical application or cutaneous, subcutaneous, intraperitoneal, parenteral, intraarterial or intravenous injection.

Alternately, one may administer the antibody in a local rather than systemic manner, for example, via injection of the antibody directly into an arthritic joint or pathogen-induced lesion characterized by immunopathology, often in a depot or sustained release formulation. Furthermore, one may administer the antibody in a targeted drug delivery system, for example, in a liposome coated with a tissue-specific antibody, targeting, for example, arthritic joint or pathogen-induced lesion characterized by immunopathology. The liposomes will be targeted to and taken up selectively by the afflicted tissue.

Selecting an administration regimen for a therapeutic depends on several factors, including the serum or tissue turnover rate of the entity, the level of symptoms, the immunogenicity of the entity, and the accessibility of the target cells in the biological matrix. Preferably, an administration regimen maximizes the amount of therapeutic delivered to the patient consistent with an acceptable level of side effects. Accordingly, the amount of biologic delivered depends in part on the particular entity and the severity of the condition being treated. Guidance in selecting appropriate doses of antibodies, cytokines, and small molecules are available. See, e.g., Wawrzynczak (1996) *Antibody Therapy*, Bios Scientific Pub. Ltd, Oxfordshire, UK; Kresina (ed.) (1991) *Monoclonal Antibodies, Cytokines and Arthritis*, Marcel Dekker, New York, N.Y.; Bach (ed.) (1993) *Monoclonal Antibodies and Peptide Therapy in Autoimmune Diseases*, Marcel Dekker, New York, N.Y.; Baert et al. (2003) *New Engl. J. Med.* 348: 601-608; Milgrom et al. (1999) *New Engl. J. Med.* 341:1966-1973; Slamon et al. (2001) *New Engl. J. Med.* 344:783-792; Beniaminovitz et al. (2000) *New Engl. J. Med.* 342:613-619; Ghosh et al. (2003) *New Engl. J. Med.* 348:24-32; Lipsky et al. (2000) *New Engl. J. Med.* 343:1594-1602.

Determination of the appropriate dose is made by the clinician, e.g., using parameters or factors known or suspected in the art to affect treatment or predicted to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced. Preferably, a biologic that will be used is substantially derived from the same species as the animal targeted for treatment (e.g. a humanized antibody for treatment of human subjects), thereby minimizing any immune response to the reagent.

Antibodies, antibody fragments, and cytokines can be provided by continuous infusion, or by doses at intervals of, e.g., one day, 1-7 times per week, one week, two weeks, monthly, bimonthly, etc. Doses may be provided, e.g., intravenously, subcutaneously, topically, orally, nasally, rectally, intramuscular, intracerebrally, intraspinally, or by inhalation. A preferred dose protocol is one involving the maximal dose or dose frequency that avoids significant undesirable side effects. A total weekly dose is generally at least 0.05 µg/kg, 0.2 µg/kg, 0.5 µg/kg, 1 µg/kg, 10 µg/kg, 100 µg/kg, 0.2 mg/kg, 1.0 mg/kg, 2.0 mg/kg, 10 mg/kg, 25 mg/kg, 50 mg/kg body weight or more. See, e.g., Yang et al. (2003) *New Engl. J. Med.* 349:427-434; Herold et al. (2002) *New Engl. J. Med.* 346: 1692-1698; Liu et al. (1999) *J. Neurol. Neurosurg. Psych.* 67:451-456; Portielji et al. (20003) *Cancer Immunol. Immunother.* 52:133-144. The desired dose of a small molecule therapeutic, e.g., a peptide mimetic, natural product, or organic chemical, is about the same as for an antibody or polypeptide, on a moles/kg basis.

As used herein, "inhibit" or "treat" or "treatment" includes a postponement of development of the symptoms associated with autoimmune disease or pathogen-induced immunopathology and/or a reduction in the severity of such symptoms that will or are expected to develop. The terms further include ameliorating existing uncontrolled or unwanted autoimmune-related or pathogen-induced immunopathology symptoms, preventing additional symptoms, and ameliorating or preventing the underlying causes of such symptoms. Thus, the terms denote that a beneficial result has been conferred on a vertebrate subject with an autoimmune or pathogen-induced immunopathology disease or symptom, or with the potential to develop such a disease or symptom.

As used herein, the term "therapeutically effective amount" or "effective amount" refers to an amount of an IL-23R-specific binding compound, e.g. and antibody, that when administered alone or in combination with an additional therapeutic agent to a cell, tissue, or subject is effective to prevent or ameliorate the autoimmune disease or pathogen-induced immunopathology associated disease or condition or the progression of the disease. A therapeutically effective dose further refers to that amount of the compound sufficient to result in amelioration of symptoms, e.g., treatment, healing, prevention or amelioration of the relevant medical condition, or an increase in rate of treatment, healing, prevention or amelioration of such conditions. When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially or simultaneously. An effective amount of therapeutic will decrease the symptoms typically by at least 10%; usually by at least 20%; preferably at least about 30%; more preferably at least 40%, and most preferably by at least 50%.

Methods for co-administration or treatment with a second therapeutic agent, e.g., a cytokine, antibody, steroid, chemotherapeutic agent, antibiotic, or radiation, are well known in the art, see, e.g., Hardman et al. (eds.) (2001) *Goodman and Gilman's The Pharmacological Basis of Therapeutics*, 10$^{th}$ ed., McGraw-Hill, New York, N.Y.; Poole and Peterson (eds.) (2001) *Pharmacotherapeutics for Advanced Practice: A Practical Approach*, Lippincott, Williams & Wilkins, Phila., Pa.; Chabner and Longo (eds.) (2001) *Cancer Chemotherapy and Biotherapy*, Lippincott, Williams & Wilkins, Phila., Pa. The pharmaceutical composition of the invention may also contain other immunosuppressive or immunomodulating agents. Any suitable immunosuppressive agent can be employed, including but not limited to anti-inflammatory agents, corticosteroids, cyclosporine, tacrolimus (i.e., FK-506), sirolimus, interferons, soluble cytokine receptors (e.g., sTNRF and sIL-1R), agents that neutralize cytokine activity (e.g., inflixmab, etanercept), mycophenolate mofetil, 15-deoxyspergualin, thalidomide, glatiramer, azathioprine, leflunomide, cyclophosphamide, methotrexate, and the like. The pharmaceutical composition can also be employed with other therapeutic modalities such as phototherapy and radiation.

Typical veterinary, experimental, or research subjects include monkeys, dogs, cats, rats, mice, rabbits, guinea pigs, horses, and humans.

VII. Antibody Production

In one embodiment, for recombinant production of the antibodies of the present invention, the nucleic acids encoding the two chains are isolated and inserted into one or more replicable vectors for further cloning (amplification of the DNA) or for expression. DNA encoding the monoclonal antibody is readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence. In one embodiment, both the light and heavy chains of a humanized anti-IL-23R antibody of the present invention are expressed from the same vector, e.g. a plasmid or an adenoviral vector.

Antibodies of the present invention may be produced by any method known in the art. In one embodiment, antibodies are expressed in mammalian or insect cells in culture, such as chinese hamster ovary (CHO) cells, human embryonic kidney (HEK) 293 cells, mouse myeloma NSO cells, baby hamster kidney (BHK) cells, *Spodoptera frugiperda* ovarian (Sf9) cells. In one embodiment, antibodies secreted from CHO cells are recovered and purified by standard chromatographic methods, such as protein A, cation exchange, anion exchange, hydrophobic interaction, and hydroxyapatite chromatography. In one embodiment, resulting antibodies are concentrated and stored in 20 mM sodium acetate, pH 5.5.

In another embodiment, the antibodies of the present invention are produced in yeast according to the methods described in WO2005/040395. Briefly, vectors encoding the individual light or heavy chains of an antibody of interest are introduced into different yeast haploid cells, e.g. different mating types of the yeast *Pichia pastoris*, which yeast haploid cells are optionally complementary auxotrophs. The transformed haploid yeast cells can then be mated or fused to give a diploid yeast cell capable of producing both the heavy and the light chains. The diploid strain is then able to secret the fully assembled and biologically active antibody. The relative expression levels of the two chains can be optimized, for example, by using vectors with different copy number, using transcriptional promoters of different strengths, or inducing expression from inducible promoters driving transcription of the genes encoding one or both chains.

In one embodiment, the respective heavy and light chains of a plurality of different anti-IL-23R antibodies (the "original" antibodies) are introduced into yeast haploid cells to create a library of haploid yeast strains of one mating type expressing a plurality of light chains, and a library of haploid yeast strains of a different mating type expressing a plurality of heavy chains. These libraries of haploid strains can be mated (or fused as spheroplasts) to produce a series of diploid yeast cells expressing a combinatorial library of antibodies comprised of the various possible permutations of light and heavy chains. The combinatorial library of antibodies can then be screened to determine whether any of the antibodies has properties that are superior (e.g. higher affinity for IL-23R) to those of the original antibodies. See. e.g., WO2005/040395.

In another embodiment, antibodies of the present invention are human domain antibodies in which portions of an antibody variable domain are linked in a polypeptide of molecular weight approximately 13 kDa. See, e.g., U.S. Pat. Publication No. 2004/0110941. Such single domain, low molecular weight agents provide numerous advantages in terms of ease of synthesis, stability, and route of administration.

VIII. Uses

The present invention provides methods for using anti-IL-23R antibodies and fragments thereof for the treatment and diagnosis of inflammatory disorders and conditions, e.g., of the central nervous system, peripheral nervous system, and gastrointestinal tract, as well as autoimmune and proliferative disorders.

Methods are provided for the treatment of, e.g., multiple sclerosis (MS), including relapsing-remitting MS and primary progressive MS, Alzheimer's disease, amyotrophic lateral sclerosis (a.k.a. ALS; Lou Gehrig's disease), ischemic brain injury, prion diseases, and HIV-associated dementia. Also provided are methods for treating neuropathic pain, posttraumatic neuropathies, Guillain-Barre syndrome (GBS), peripheral polyneuropathy, and nerve regeneration.

Provided are methods for treating or ameliorating one or more of the following features, symptoms, aspects, manifestations, or signs of multiple sclerosis, or other inflammatory disorder or condition of the nervous system: brain lesions, myelin lesions, demyelination, demyelinated plaques, visual disturbance, loss of balance or coordination, spasticity, sensory disturbances, incontinence, pain, weakness, fatigue, paralysis, cognitive impairment, bradyphrenia, diplopia, optic neuritis, paresthesia, gait ataxia, fatigue, Uhtoff's symptom, neuralgia, aphasia, apraxia, seizures, visual-field loss, dementia, extrapyramidal phenomena, depression, sense of well-being, or other emotional symptoms, chronic progressive myelopathy, and a symptom detected by magnetic resonance imaging (MRI), including gadolinium-enhancing lesions, evoked potential recordings, or examination of cerebrospinal fluid. See, e.g., Kenealy et al. (2003) *J. Neuroimmunol.* 143:7-12; Noseworthy et al. (2000) *New Engl. J. Med.* 343:938-952; Miller et al. (2003) *New Engl. J. Med.* 348:15-23; Chang et al. (2002) *New Engl. J. Med.* 346:165-173; Bruck and Stadelmann (2003) *Neurol. Sci.* 24 Suppl.5:S265-S267.

Moreover, the present invention provides methods for treating and diagnosing inflammatory bowel disorders, e.g., Crohn's disease, ulcerative colitis, celiac disease, and irritable bowel syndrome. Provided are methods for treating or ameliorating one or more of the following symptoms, aspects, manifestations, or signs of an inflammatory bowel disorder: malabsorption of food, altered bowel motility, infection, fever, abdominal pain, diarrhea, rectal bleeding, weight loss, signs of malnutrition, perianal disease, abdominal mass, and growth failure, as well as intestinal complications such as stricture, fistulas, toxic megacolon, perforation, and cancer, and including endoscopic findings, such as, friability, apthhous and linear ulcers, cobblestone appearance, pseudopolyps, and rectal involvement and, in addition, anti-yeast antibodies. See, e.g., Podolsky, supra; Hanauer, supra; Horwitz and Fisher, supra.

Also contemplated is treatment of inflammatory disorders such as psoriasis, atopic dermatitis, arthritis, including rheumatoid arthritis, osteoarthritis, and psoriatic arthritis, autoimmune disorders, such as systemic lupus erythematosus and type I diabetes, and proliferative disorders such as cancer. See, e.g., PCT patent application publications WO 04/081190; WO 04/071517; WO 00/53631; and WO 01/18051.

The IL-23R binding compounds of the present invention can also be used in combination with one or more antagonists of other cytokines (e.g. antibodies), including but not limited to, IL-23p19, IL-17A, IL-17F, TNF-α, IL-1β, IL-6 and TGF-β. See, e.g., Veldhoen (2006) *Immunity* 24:179-189; Dong (2006) *Nat. Rev. Immunol.* 6(4):329-333. In various embodiments, an IL-23R binding compound of the invention is administered before, concurrently with, or after administration of the another antagonist or antagonists, such as an anti-IL-17A antibody. In one embodiment, an IL-17A binding compound is used in treatment of the acute early phase of an adverse immune response (e.g. MS, Crohn's Disease) alone or in combination with an IL-23R antagonist antibody of the present invention. In the latter case, the IL-17A binding compound may be gradually decreased and treatment with the antagonist of IL-23R alone is continued to maintain suppression of the adverse response. Alternatively, antagonists to IL-23p19, IL-1β, IL-6 and/or TGF-β may be administered concurrently, before or after an IL-23R binding compound of the present invention. See Cua and Kastelein (2006) *Nat. Immunol.* 7:557-559; Tato and O'Shea (2006) *Nature* 441: 166-168; Iwakura and Ishigame (2006) *J. Clin. Invest.* 116: 1218-1222.

The broad scope of this invention is best understood with reference to the following examples, which are not intended to limit the inventions to the specific embodiments. The specific embodiments described herein are offered by way of example only, and the invention is to be limited by the terms of the appended claims, along with the full scope of equivalents to which such claims are entitled.

EXAMPLES

Example 1

General Methods

Standard methods in molecular biology are described. Maniatis et al. (1982) *Molecular Cloning, A Laboratory Manual*, Cold Spring Harbor Laboratory Press, Cold Spring Harbor, N.Y.; Sambrook and Russell (2001) *Molecular Cloning, 3rd ed.*, Cold Spring Harbor Laboratory Press, Cold Spring Harbor, N.Y.; Wu (1993) *Recombinant DNA*, Vol. 217, Academic Press, San Diego, Calif. Standard methods also appear in Ausbel et al. (2001) *Current Protocols in Molecular Biology*, Vols.1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described. Coligan et al. (2000) *Current Protocols in Protein Science*, Vol. 1, John Wiley and Sons, Inc., New York. Chemical analysis, chemical modification, post-translational modification, production of fusion proteins, glycosylation of proteins are described. See, e.g., Coligan et al. (2000) *Current Protocols in Protein Science*, Vol. 2, John Wiley and Sons, Inc., New York; Ausubel et al. (2001) *Current Protocols in Molecular Biology*, Vol. 3, John Wiley and Sons, Inc., NY, N.Y., pp. 16.0.5-16.22.17; Sigma-Aldrich, Co. (2001) *Products for Life Science Research*, St. Louis, Mo.; pp. 45-89; Amersham Pharmacia Biotech (2001) *BioDirectory*, Piscataway, N.J., pp. 384-391. Production, purification, and fragmentation of polyclonal and monoclonal antibodies are described. Coligan et al. (2001) *Current Protcols in Immunology*, Vol. 1, John Wiley and Sons, Inc., New York; Harlow and Lane (1999) *Using Antibodies*, Cold Spring Harbor Laboratory Press, Cold Spring Harbor, N.Y.; Harlow and Lane, supra. Standard techniques for characterizing ligand/receptor interactions are available. See, e.g., Coligan et al. (2001) *Current Protcols in Immunology*, Vol. 4, John Wiley, Inc., New York.

Methods for flow cytometry, including fluorescence activated cell sorting detection systems (FACS®), are available. See, e.g., Owens et al. (1994) *Flow Cytometry Principles for Clinical Laboratory Practice*, John Wiley and Sons, Hoboken, N.J.; Givan (2001) *Flow Cytometry, 2nd ed.*; Wiley-Liss, Hoboken, N.J.; Shapiro (2003) *Practical Flow Cytometry*, John Wiley and Sons, Hoboken, N.J. Fluorescent reagents suitable for modifying nucleic acids, including nucleic acid primers and probes, polypeptides, and antibodies, for use, e.g., as diagnostic reagents, are available. Molecular Probes (2003) *Catalogue*, Molecular Probes, Inc., Eugene, Oreg.; Sigma-Aldrich (2003) *Catalogue*, St. Louis, Mo.

Standard methods of histology of the immune system are described. See, e.g., Muller-Harmelink (ed.) (1986) *Human Thymus: Histopathology and Pathology*, Springer Verlag, New York, N.Y.; Hiatt, et al. (2000) *Color Atlas of Histology*, Lippincott, Williams, and Wilkins, Phila, Pa.; Louis, et al. (2002) *Basic Histology: Text and Atlas*, McGraw-Hill, New York, N.Y.

Software packages and databases for determining, e.g., antigenic fragments, leader sequences, protein folding, functional domains, glycosylation sites, and sequence alignments, are available. See, e.g., GenBank, Vector NTI® Suite (Informax, Inc, Bethesda, Md.); GCG Wisconsin Package (Accelrys, Inc., San Diego, Calif.); DeCypher® (TimeLogic Corp., Crystal Bay, Nev.); Menne et al. (2000) *Bioinformatics* 16: 741-742; Menne et al. (2000) *Bioinformatics Applications Note* 16:741-742; Wren et al. (2002) *Comput. Methods Programs Biomed.* 68:177-181; von Heijne (1983) *Eur. J. Biochem.* 133:17-21; von Heijne (1986) *Nucleic Acids Res.* 14:4683-4690.

Example 2

Generation and Humanization of Anti-human IL-23R Antibodies

Anti-human IL-23R antibodies are generated by immunizing rats or mice with the extracellular domain of human-IL-23R (residues 24-353 of SEQ ID NO: 41), either with a C-terminal histidine tag or as an Ig (human IgG1 Fc) fusion protein. Monoclonal antibodies are then prepared by standard methods.

The humanization of antibodies is described generally, e.g., in PCT patent application publications WO 2005/047324 and WO 2005/047326. Exemplary humanized heavy- and light-chain variable domain sequences are provided at FIGS. 1 and 2, respectively, and in the Sequence Listing.

Briefly, the amino acid sequence of the non-human VH domain (e.g. SEQ ID NOs: 1-5) is compared to a group of five human VH germline amino acid sequences; one representative from subgroups IGHV1 and IGHV4 and three representatives from subgroup IGHV3. The VH subgroups are listed in M.-P. Lefranc (2001) "Nomenclature of the Human Immunoglobulin Heavy (IGH) Genes", *Experimental and Clinical Immunogenetics* 18:100-116. The framework sequences of the human germline sequence with the closest match are used to construct a humanized VH domain.

The rodent anti-huIL-23R antibodies disclosed herein are all of the kappa subclass of VL. The amino acid sequences of the non-human VL domain (e.g. SEQ ID NOs: 6-10) is compared to a group of four human VL kappa germline amino acid sequences. The group of four is comprised of one representative from each of four established human VL subgroups listed in V. Barbie & M.-P. Lefranc (1998) "The Human Immunoglobulin Kappa Variable (IGKV) Genes and Joining (IGKJ) Segments", *Experimental and Clinical Immunogenetics* 15:171-183 and M.-P. Lefranc (2001) "Nomenclature of the Human Immunoglobulin Kappa (IGK) Genes", *Experimental and Clinical Immunogenetics* 18:161-174. The four subgroups also correspond to the four subgroups listed in Kabat et al. (1991-5th Ed.) "Sequences of Proteins of Immunological Interest", U. S. Department of Health and Human Services, NIH Pub. 91-3242, pp. 103-130. The framework sequences of the human germline sequence with the closest match are used to construct a humanized VL domain.

Based on the foregoing analysis, a humanized form of mouse antibody clone 20D7 is constructed using human heavy chain sequence from subgroup I (germline sequence DP-14). The sequence of the resulting humanized heavy chain variable domain (hu20D7-a) is provided at SEQ ID NO: 45. A variant of hu20D7-a, hu20D7-b (SEQ ID NO: 46), is identical except for a T72L substitution. A second variant, hu20D7-c (SEQ ID NO: 47), is identical to hu20D7-b except for an M70F substitution. Both of these sequence variations are in the framework region between CDRH2 and CDRH3, and are illustrated as bold type-face residues in FIG. 1. A full-length humanized heavy chain, comprising the hu20D7-c variable domain and a human IgG1 constant domain, is provided at SEQ ID NO: 50.

Light chain variable domain sequences are also constructed from mouse antibody clone 20D7. One light chain variable domain sequence, hu20D7-IV (SEQ ID NO: 48), comprises the CDR sequences of the parental mouse antibody and human light chain framework sequences from light chain subgroup IV (germline sequence Z-B3). Another light chain variable domain sequence, hu20D7-II-a (SEQ ID NO: 49), comprises the CDR sequences of the parental mouse antibody and human light chain framework sequences from light chain subgroup II (germline sequence Z-A19). An additional light chain variable domain sequence variant (hu20D7-II-b) is provided at SEQ ID NO:53, in which the serine residue at position 32 is replaced by threonine (S32T). The serine is replaced to reduce the likelihood of deamidation of the preceding asparagine residue. See Bischoff & Kolbe (1994) *J. Chromatog.* 662:261. All three light chain variable domain sequences are presented in FIG. 2. Full-length humanized light chains, comprising the hu20D7-II-a and hu20D7-II-b variable domains in the context of human kappa light chains, are provided at SEQ ID NOs: 51 and 54, respectively.

Any pairwise combination of the humanized heavy and light chains described in this example (e.g. the hu20D7-II-b light chain and the hu20D7-c heavy chain) can be used to create a functional anti-human-IL-23R antibody. Full-length heavy and light chains can be constructed from any of the variable domains disclosed herein by analogy with the construction of SEQ ID NOs: 50 and 51 from SEQ ID NOs: 47 and 49, respectively. Alternatively, other heavy chain constant domains (e.g. $IgG_2$) or other light chains (e.g. lambda) may be constructed using known human immunoglobulin sequences.

Once the target amino acid sequences of the variable heavy and light chains are determined, plasmids encoding the full-length humanized antibody may be generated. Plasmid sequences may be altered using Kunkel mutagenesis (see, e.g., Kunkel T A. (1985) *Proc. Natl. Acad. Sci. U.S.A.* 82:488-492) to change the DNA sequence to the target humanized antibody sequences. Simultaneously, codon optimization may be performed to provide for potentially optimal expression. Sequence optimization may also be performed by commercial vendors, such as GENEART, Inc., Toronto, ON, Canada.

In the case of the humanization of the 20D7 antibody, simple substitution of the best-match human germline frameworks into the rodent variable domains produced antibodies (e.g. SEQ ID NO: 45 paired with SEQ ID NO: 48 or 49) with substantially reduced binding affinity for IL-23R when compared with the parental (rodent) forms. To determine the source of the reduced affinity, hemichimeric constructs were created in which the humanized light and heavy chains were paired with chimeric heavy and light chains, respectively. Chimeric chains include the rodent variable domain and a human constant domain. It had been previously determined earlier that chimeric forms of the 20D7 antibodies retained essentially the same affinity as the parental rodent antibody. It was observed that the hemichimeric antibody with the humanized heavy chain had reduced binding, whereas the hemichimeric antibody with the humanized light chain retained the affinity of the parental antibody, indicating that the problem was with the humanized heavy chain. The humanized heavy chain was then scrutinized to find positions at which the humanized framework sequences differed from the parental (rodent) framework sequences, which positions were considered likely causes of the reduced affinity. Sequence variants were produced at several positions, and heavy chains having T72L and M70F substitutions were found to substantially improve binding affinity. See Example 4, infra. See, e.g., Tramontano et al. (1990) *J. Mol. Biol.* 215:175. (Note that unless otherwise indicated, sequence numbering in this patent application relates to the numbering of the sequence listing, and not to alternative numbering schemes such as the Kabat system.)

A humanized form of rat antibody clone 8B10 is constructed in a similar fashion, using human heavy chain sequence from subgroup III (germline sequence DP-46). The sequence of the resulting humanized heavy chain variable domain (hu8B10) is provided at SEQ ID NO: 57. Variants of hu8B10 heavy chain variable domain may be created to improve binding affinity or otherwise improve the properties of the resulting antibody. For example, the asparagine residue at position 30 of SEQ ID NO: 57 (in CDRH1) may be changed to threonine (N30T) to improve binding affinity. Framework residues may also be altered, such as residues A24, E46, W47, N76, N79, L81, or R100. Exemplary framework changes include E46D and W47L.

Light chain variable domain sequences are also constructed from rat antibody clone 8B10. A hu8B10 light chain variable domain sequence comprising the CDR sequences of the parental rat antibody and human light chain framework sequences from light chain subgroup kappa-1 (germline sequence Z-012) is provided at SEQ ID NO: 58.

Example 3

Determining the Equilibrium Dissociation Constant ($K_d$) for Anti-human IL-23R Antibodies Using KinExA Technology The equilibrium dissociation constants ($K_d$) for anti human IL-23R antibodies are determined using the KinExA 3000 instrument. Sapidyne Instruments Inc., Boise Id., USA KinExA uses the principle of the Kinetic Exclusion Assay method based on measuring the concentration of uncomplexed antibody in a mixture of antibody, antigen and antibody-antigen complex. The concentration of free antibody is measured by exposing the mixture to a solid-phase immobilized antigen for a very brief period of time. In practice, this is accomplished by flowing the solution phase antigen-antibody mixture past antigen-coated particles trapped in a flow cell. Data generated by the instrument are analyzed using custom software. Equilibrium constants are calculated using a mathematical theory based on the following assumptions:

1. The binding follows the reversible binding equation for equilibrium:

$$k_{on}[Ab][Ag]=k_{off}[AbAg]$$

2. Antibody and antigen bind 1:1 and total antibody equals antigen-antibody complex plus free antibody.

3. Instrument signal is linearly related to free antibody concentration.

PMMA particles (Sapidyne, Cat No. 440198) are coated with biotinylated IL-23R (or a fragment thereof, such as the extracellular domain) according to Sapidyne "Protocol for coating PMMA particles with biotinylated ligands having short or nonexistent linker arms." EZ-link TFP PEO-biotin (Pierce, Cat. No. 21219) is used to make biotinylated IL-23R, as per the manufacturer's recommendations (Pierce bulletin 0874).

Antibody r8B10 showed a $K_d$ of $4.2 \times 10^{-11}$ M, and antibody m20D7 showed a $K_d$ of $9 \times 10^{-12}$ M, for binding to human IL-23R as determined by KinExA analysis.

Example 4

Determining the Equilibrium Dissociation Constant ($K_d$) for Humanized Anti-human IL-23R Antibodies Using BIAcore® Label-Free Interaction Analysis System Technology BIAcore® label-free interaction analysis system determinations are performed essentially as described at Example 4 of U.S. Patent Application Publication No. 2007/0048315. Briefly, ligands (anti-IL-23R mAbs) are immobilized on a BIAcore® label-free interaction analysis system CM5 sensor chip using standard amine-coupling procedure. Kinetic constants for the various interactions are determined using BIAevaluation software 3.1. The $K_d$ is determined using the calculated dissociation and association rate constants.

BIAcore® label-free interaction analysis system determinations of the $K_d$ for the mouse 20D7 antibody for human IL-23R showed that replacement of mouse framework sequences with human framework sequences (hu20D7-a, SEQ ID NO: 45) reduced binding affinity by approximately 50-fold, from approximately 85 pM to approximately 4300 pM. Introduction of the T72L mutation (hu20D7-b, SEQ ID NO: 46) into the heavy chain improved the $K_d$ to approximately 360 pM, and introduction of the T72L along with the M70F mutation (hu20D7-c, SEQ ID NO: 47) further improved the $K_d$ to approximately 230 pM. The mutations introduced in the hu20D7-c heavy chain thus represent an improvement of nearly 20-fold in binding affinity compared to the simple humanization without subsequent optimization.

By way of comparison, the parental rat 8B10 antibody exhibited a $K_d$ of approximately 300 pM for human IL-23R when assessed using the same assay.

Example 5

Proliferation Bioassays for the Assessment of Neutralizing Anti-IL-23R Antibodies The ability of a monoclonal antibody to biologically neutralize IL-23/IL-23R is assessed by the application of short-term proliferation bioassays that employ cells that express recombinant IL-23 receptors. The transfectant Ba/F3-2.2lo cells proliferate in response to human IL-23 and the response can be inhibited by a neutralizing anti-IL-23R antibody. The concentration of IL-23 chosen for the assay is selected to be within the linear region of the dose-response curve, near plateau and above EC50. Proliferation, or lack thereof, is measured by colorimetric means using Alamar Blue, a growth indicator dye based on detection of metabolic activity. The ability of an antibody to neutralize IL-23/IL-23R is assessed by its IC50 value, or concentration of antibody that induces half-maximal inhibition of IL-23 proliferation.

The assay is performed essentially as follows. Ba/F3 transfectants are maintained in RPMI-1640 medium, 10% fetal calf serum, 50 μM 2-mercaptoethanol, 2 mM L-Glutamine, 50 μg/mL penicillin-streptomycin, and 10 ng/mL mouse IL-3. Proliferation bioassays are performed in RPMI-1640 medium, 10% fetal calf serum, 50 μM 2-mercaptoethanol, 2 mM L-Glutamine, and 50 μg/mL penicillin-streptomycin.

Assays are performed in 96-well flat bottom plates (Falcon 3072 or similar) in 150 μL per well. Both IL-23 and anti-IL-23R antibodies are added at a series of concentrations, e.g. 1:3 serial dilutions. Titrations of the anti-IL-23R antibody of interest are optionally pre-incubated with cells prior to addition of IL-23. Bioassay plates are incubated in a humidified tissue culture chamber (37C, 5% $CO_2$) for 40-48 hr. At the end of the culture time, Alamar Blue (Biosource Cat #DAL1100) is added at 16.5 µL/well and allowed to develop for 5-12 hours. Absorbance is then read at 570 nm and 600 nm (VERSAmax Microplate Reader, Molecular Probes, Eugene, Oreg., USA), and an $OD_{570-600}$ is obtained. Duplicates are run for each sample. Absorbance is plotted against cytokine or antibody concentration using GraphPad Prism® 3.0 software (Graphpad Software Inc., San Diego, Calif., USA), and IC50 values are determined using non-linear regression (curve fit) of sigmoidal dose-response.

Example 6

Mouse Splenocyte Assay for IL-23 Based on IL-17 Production

The biological activity of anti-IL-23R antibodies of the present invention may be assessed using the mouse splenocyte assay essentially as described in Aggarwal et al. (2003) *J. Biol. Chem.* 278:1910 and Stumhofer et al. (2006) *Nature Immunol.* 7:937. The mouse splenocyte assay measures the activity of IL-23 in a sample as a level of IL-17 production by murine splenocytes. The inhibitory activity of anti-IL-23R antibodies is then assessed by determining the concentration of antibody necessary to reduce the IL-23/IL-23R activity in a given sample by 50% (the IC50). The IC50 as measured by this assay is greater than or equal to the equilibrium dissociation binding constant ($K_d$), i.e. the $K_d$ may be equal to or lower than the IC50. As always, lower IC50 and $K_d$ values reflect higher activities and affinities.

Briefly, spleens are obtained from 8-12 wk old female C57BL/6J mice (Jackson Laboratories, Bar Harbor, Me., USA). Spleens are ground, pelleted twice, and filtered through a cell strainer (70 µm nylon). The recovered cells are cultured in 96-well plates ($4 \times 10^5$ cells/well) in the presence of human IL-23 (10 ng/ml, ~170 pM) and mouse-anti-CD3e antibodies (1 µg/ml) (BD Pharmingen, Franklin Lakes, N.J., USA), with or without the anti-IL-23R antibody to be assayed. Anti IL-23R antibodies are added at a series of 3-fold dilutions. Cells are cultured for 72 hours, pelleted, and the supernatant is assayed for IL-17 levels by sandwich ELISA.

IL-17 ELISA is performed as follows. Plates are coated with a capture anti-IL-17 antibody (100 ng/well) overnight at 4° C., washed and blocked. Samples and standards are added and incubated for two hours at room temperature with shaking Plates are washed, and a biotinylated anti-IL-17 detection antibody (100 ng/well) is added and incubated for one hour at room temperature with shaking The capture and detection antibodies are different antibodies that both bind to mouse IL-17 but do not cross-block. Plates are washed, and bound detection antibody is detected using streptavidin-HRP (horseradish peroxidase) and TMB (3,3',5,5'-tetramethylbenzidine). The plate is then read at 450-650 nm and the concentration of IL-17 in samples is calculated by comparison with standards.

Example 7

Characterization of Anti-IL-23R Antibody Hum20D7

A humanized anti-IL-23R antibody is generated using the heavy chain sequence hu20D7-c and the light chain sequence hu20D7-II-b, for which sequences are provided at SEQ ID NOs: 50 and 54, respectively. The resulting antibody is referred to in this example as hum20D7. The antibody is prepared from mammalian cells using a vector harboring DNA sequences encoding the heavy and light chains, as provided at SEQ ID NOs: 55 (hu20D7-c) and 56 (hu20D7-II-b), respectively, although other DNA sequences encoding the same polypeptide sequences may also be used.

Hum20D7 has a $K_d$ of 131 pM for human IL-23R when assayed by BIAcore analysis, essentially as described in Example 4 (supra).

The biological activity of hum20D7 is also assessed using a human splenocyte assay, essentially as described in Example 6 (supra) with the exception that splenocytes are obtained from human spleens rather than mouse, no anti-CD3e antibody is used, and that IFN-γ is the readout rather than IL-17. The assay measures the activity of IL-23 in a sample by determining the level of IFN-γ production by human primary splenocytes. Human splenocytes are exposed to human IL-23 (170 pM) in the presence of various concentrations of anti-IL-23R antibody hum20D7, or in the absence of the antibody. IFN-γ is detected by sandwich ELISA. Hum20D7 exhibits an IC50 of 34 pM in the human splenocyte assay.

The biological activity of hum20D7 is further assessed using a KIT225 STAT-3 phosphorylation assay, essentially as described in Parham et al. (2002) *J. Immunol.* 168:5699. Human KIT225 cells, a leukemic T cell line, are stimulated with 138 pM human IL-23 in the presence of various concentrations of anti-IL-23R antibody hum20D7, or in the absence of the antibody. IL-23 activity is measured by detecting the level of STAT3 phosphorylation. Hum20D7 exhibits an IC50 of 34 pM in the KIT225 assay.

Table 4 provides a brief description of the sequences in the sequence listing.

TABLE 4

| SEQ ID NO: | Description |
| --- | --- |
| 1 | 41F11 Heavy Chain Variable |
| 2 | 8B10 Heavy Chain Variable |
| 3 | 3C11 Heavy Chain Variable |
| 4 | 20D7 Heavy Chain Variable |
| 5 | 20E5 Heavy Chain Variable |
| 6 | 41F11 Light Chain Variable |
| 7 | 8B10 Light Chain Variable |
| 8 | 3C11 Light Chain Variable |
| 9 | 20D7 Light Chain Variable |
| 10 | 20E5 Light Chain Variable |
| 11 | 41F11 CDRH1 |
| 12 | 8B10 CDRH1 |
| 13 | 3C11 CDRH1 |
| 14 | 20D7 CDRH1 |
| 15 | 20E5 CDRH1 |
| 16 | 41F11 CDRH2 |
| 17 | 8B10 CDRH2 |
| 18 | 3C11 CDRH2 |
| 19 | 20D7 CDRH2 |
| 20 | 20E5 CDRH2 |
| 21 | 41F11 CDRH3 |
| 22 | 8B10 CDRH3 |
| 23 | 3C11 CDRH3 |
| 24 | 20D7 CDRH3 |
| 25 | 20E5 CDRH3 |
| 26 | 41F11 CDRL1 |
| 27 | 8B10 CDRL1 |
| 28 | 3C11 CDRL1 |
| 29 | 20D7 CDRL1 |
| 30 | 20E5 CDRL1 |
| 31 | 41F11 CDRL2 |

TABLE 4-continued

| Sequence Identifiers | |
|---|---|
| SEQ ID NO: | Description |
| 32 | 8B10 CDRL2 |
| 33 | 3C11 CDRL2 |
| 34 | 20D7 CDRL2 |
| 35 | 20E5 CDRL2 |
| 36 | 41F11 CDRL3 |
| 37 | 8B10 CDRL3 |
| 38 | 3C11 CDRL3 |
| 39 | 20D7 CDRL3 |
| 40 | 20E5 CDRL3 |
| 41 | Human IL-23R |
| 42 | Murine IL-23R |
| 43 | Human IL-12Rβ1 |
| 44 | Murine IL-12Rβ1 |
| 45 | hu20D7-a Heavy Chain Variable |
| 46 | hu20D7-b Heavy Chain Variable |
| 47 | hu20D7-c Heavy Chain Variable |
| 48 | hu20D7-IV Light Chain Variable |
| 49 | hu20D7-II-a Light Chain Variable |
| 50 | hu20D7-c Heavy Chain |
| 51 | hu20D7-II-a Light Chain |
| 52 | hu20D7-II-b CDRL1 |
| 53 | hu20D7-II-b Light Chain Variable |
| 54 | hu20D7-II-b Light Chain |
| 55 | hu20D7-c Heavy Chain DNA |
| 56 | hu20D7-II-b Light Chain DNA |
| 57 | hu8B10 Heavy Chain Variable |
| 58 | hu8B10 Light Chain Variable |

What is claimed is:

1. An isolated nucleic acid encoding at least one of the antibody light chain variable domain or the antibody heavy chain variable domain of a binding compound that binds to human IL-23R, wherein:
   a) the antibody light chain variable domain comprises CDRL1, CDRL2 and CDRL3, wherein:
      CDRL1 comprises the sequence of SEQ ID NO: 29 or 52;
      CDRL2 comprises the sequence of SEQ ID NO: 34; and
      CDRL3 comprises the sequence of SEQ ID NO: 39; and
   b) the antibody heavy chain variable domain comprises CDRH1, CDRH2 and CDRH3, wherein:
      CDRH1 comprises the sequence of SEQ ID NO: 14;
      CDRH2 comprises the sequence of SEQ ID NO: 19; and
      CDRH3 comprises the sequence of SEQ ID NO: 24.

2. An isolated nucleic acid encoding at least one of the antibody light chain variable domain or the antibody heavy chain variable domain of a binding compound that binds to human IL-23R, wherein:
   a) the antibody light chain variable domain consists essentially of a sequence selected from the group consisting of SEQ ID NOs: 48, 49 and 53; and
   b) the antibody heavy chain variable domain consists essentially of a sequence selected from the group consisting of SEQ ID NOs: 45, 46 and 47.

3. An expression vector comprising the nucleic acid of either of claims 1 and 2 operably linked to control sequences that are recognized by a host cell when the host cell is transfected with the vector, wherein the expression vector comprises nucleic acid sequences encoding at least the variable domains of both the light chain and the heavy chain of the binding compound.

4. An isolated host cell comprising the expression vector of claim 3.

5. A method of producing an antibody that binds to human IL-23R, or antigen binding fragment thereof, which is encoded by the nucleic acid of the expression vector of the host cell of claim 4, said method comprising:
   a) culturing the host cell of claim 4 in culture medium under conditions wherein the nucleic acid sequences are expressed, thereby producing the antibody, or antigen binding fragment thereof; and
   b) recovering the antibody, or antigen binding fragment thereof, from the host cell or culture medium.

6. An isolated host cell comprising:
   a) a first expression vector comprising the nucleic acid of either of claims 1 and 2 encoding the variable domain of the light chain of the binding compound; and
   b) a second expression vector comprising the nucleic acid of either of claims 1 and 2 encoding the variable domain of the heavy chain of the binding compound.

7. A method of producing an antibody that binds to human IL-23R, or antigen binding fragment thereof, which is encoded by the nucleic acids of the expression vectors of the host cell of claim 6, said method comprising:
   a) culturing the host cell of claim 6 in culture medium under conditions wherein the nucleic acid sequence is sequences are expressed, thereby producing the antibody, or antigen binding fragment thereof; and
   b) recovering the antibody, or antigen binding fragment thereof, from the host cell or culture medium.

8. An isolated nucleic acid encoding at least one of the antibody light chain or the antibody heavy chain of a first binding compound that binds to the same epitope of human IL-23R as a second binding compound comprising:
   a) an antibody light chain comprising the sequence of SEQ ID NO: 54; and
   b) an antibody heavy chain comprising the sequence of SEQ ID NO: 50.

9. An expression vector comprising the nucleic acid of claim 8 operably linked to control sequences that are recognized by a host cell when the host cell is transfected with the vector, wherein the expression vector comprises nucleic acid sequences encoding both the light chain and the heavy chain of the first binding compound.

10. An isolated host cell comprising the expression vector of claim 9.

11. A method of producing an antibody that binds to human IL-23R, or antigen binding fragment thereof, which is encoded by the nucleic acid of the expression vector of the host cell of claim 10, said method comprising:
   a) culturing the host cell of claim 10 in culture medium under conditions wherein the nucleic acid sequences are expressed, thereby producing the antibody, or antigen binding fragment thereof; and
   b) recovering the antibody, or antigen binding fragment thereof, from the host cell or culture medium.

12. An isolated host cell comprising:
   a) first expression vector comprising the nucleic acid of claim 8 encoding the light chain of the first binding compound; and
   b) a second expression vector comprising the nucleic acid of claim 8 encoding the heavy chain of the first binding compound.

13. A method of producing an antibody that binds to human IL-23R, or antigen binding fragment thereof, which is encoded by the nucleic acids of the expression vectors of the host cell of claim 12, said method comprising:
   a) culturing the host cell of claim 12 in culture medium under conditions wherein the nucleic acid sequences are expressed, thereby producing the antibody, or antigen binding fragment thereof; and
   b) recovering the antibody, or antigen binding fragment thereof, from the host cell or culture medium.

14. An isolated nucleic acid encoding at least one of the antibody light chain variable domain or the antibody heavy chain variable domain of a binding compound that binds to human IL-23R, wherein:
   a) the antibody light chain variable domain comprises a sequence selected from the group consisting of SEQ ID NOs: 48, 49 and 53; and
   b) the antibody heavy chain variable domain comprises a sequence selected from the group consisting of SEQ ID NOs: 45, 46 and 47.

15. An isolated nucleic acid encoding at least one of the antibody light chain variable domain or the antibody heavy chain variable domain of a binding compound that binds to human IL-23R, wherein:
   a) the antibody light chain variable domain comprises the sequence of SEQ ID NO: 53, and
   b) the antibody heavy chain variable domain comprises the sequence of SEQ ID NO: 47.

16. An isolated nucleic acid encoding at least one of the antibody light chain or the antibody heavy chain of a binding compound that binds to human IL-23R, wherein:
   a) the antibody light chain comprises the sequence of SEQ ID NO: 54; and
   b) the antibody heavy chain comprises the sequence of SEQ ID NO: 50.

17. An isolated nucleic acid encoding at least one of the antibody light chain variable domain or the antibody heavy chain variable domain of a binding compound that binds to the same epitope of human IL-23R as the antibody produced by the hybridoma deposited with ATCC under accession number PTA-7801.

* * * * *

SEQUENCE LISTING

```
<160> NUMBER OF SEQ ID NOS: 58

<210> SEQ ID NO 1
<211> LENGTH: 117
<212> TYPE: PRT
<213> ORGANISM: Rattus norvegicus
<220> FEATURE:
<221> NAME/KEY: CDRH1
<222> LOCATION: (26)..(35)
<220> FEATURE:
<221> NAME/KEY: CDRH2
<222> LOCATION: (50)..(66)
<220> FEATURE:
<221> NAME/KEY: CDRH3
<222> LOCATION: (99)..(106)

<400> SEQUENCE: 1

Glu Val Gln Leu Val Glu Ser Gly Gly Gly Leu Val Gln Pro Gly Arg
1               5                   10                  15

Ser Leu Lys Leu Ser Cys Val Ala Ser Gly Phe Thr Phe Asn Asn Ser
            20                  25                  30

Trp Met Thr Trp Ile Arg Gln Ala Pro Gly Lys Gly Leu Glu Cys Val
        35                  40                  45

Ala Ser Ile Thr Asn Thr Gly Gly Ser Thr Tyr Tyr Pro Asp Ser Val
    50                  55                  60

Lys Gly Arg Phe Thr Ile Ser Arg Asp Asn Ala Lys Ser Thr Leu Tyr
65                  70                  75                  80

Leu Gln Met Asn Ser Leu Arg Ser Glu Asp Thr Ala Thr Tyr Tyr Cys
                85                  90                  95

Ser Arg Glu Asp Asn Ser Gly Tyr Asp Tyr Trp Gly Gln Gly Val Met
            100                 105                 110

Val Thr Val Ser Ser
        115

<210> SEQ ID NO 2
<211> LENGTH: 119
<212> TYPE: PRT
<213> ORGANISM: Rattus norvegicus
<220> FEATURE:
<221> NAME/KEY: CDRH1
<222> LOCATION: (26)..(35)
<220> FEATURE:
<221> NAME/KEY: CDRH2
<222> LOCATION: (50)..(68)
<220> FEATURE:
```

```
<221> NAME/KEY: CDRH3
<222> LOCATION: (101)..(108)

<400> SEQUENCE: 2

Glu Val Lys Leu Val Glu Ser Gly Gly Gly Leu Glu Gln Pro Lys Gly
 1               5                  10                  15

Ser Leu Lys Leu Ser Cys Thr Val Ser Gly Phe Asp Phe Asn Ser Tyr
            20                  25                  30

Gly Met Ser Trp Val Arg Gln Ala Pro Gly Lys Gly Leu Asp Leu Val
        35                  40                  45

Ala Asp Ile Asn Ser Lys Ser Tyr Asn Tyr Ala Thr Tyr Tyr Ala Asp
    50                  55                  60

Ser Val Lys Asp Arg Phe Thr Ile Ser Arg Asp Ser Gln Ser Met
65                  70                  75                  80

Val Tyr Leu Glu Met Asp Asn Leu Lys Thr Glu Asp Thr Ala Leu Tyr
                85                  90                  95

Tyr Cys Thr Val His His Ser Asp Tyr Phe Glu Tyr Trp Gly Gln Gly
            100                 105                 110

Val Met Val Thr Val Ser Ser
        115

<210> SEQ ID NO 3
<211> LENGTH: 128
<212> TYPE: PRT
<213> ORGANISM: Rattus norvegicus
<220> FEATURE:
<221> NAME/KEY: CDRH1
<222> LOCATION: (26)..(37)
<220> FEATURE:
<221> NAME/KEY: CDRH2
<222> LOCATION: (52)..(67)
<220> FEATURE:
<221> NAME/KEY: CDRH3
<222> LOCATION: (100)..(117)

<400> SEQUENCE: 3

Gln Val Thr Leu Lys Glu Ser Gly Pro Gly Ile Leu Gln Pro Ser Gln
 1               5                  10                  15

Thr Leu Ser Leu Thr Cys Thr Phe Ser Gly Phe Ser Leu Ser Thr Tyr
            20                  25                  30

Gly Met Gly Val Gly Trp Ile Arg Gln Pro Ser Gly Lys Gly Leu Glu
        35                  40                  45

Trp Leu Ala Asn Ile Trp Trp Asp Asp Asp Lys Tyr Tyr Asn Pro Ser
    50                  55                  60

Leu Lys Asn Arg Leu Thr Ile Ser Lys Asp Thr Ser Asn Asn Gln Ala
65                  70                  75                  80

Phe Leu Lys Ile Thr Asn Val Asp Thr Ala Asp Thr Ala Thr Tyr Tyr
                85                  90                  95

Cys Ala Arg Ile Asp Ala His Pro Met Gly Ile Thr Thr Pro Asp Tyr
            100                 105                 110

Tyr Val Val Asp Ala Trp Gly Gln Gly Ala Ser Val Thr Val Ser Ser
        115                 120                 125

<210> SEQ ID NO 4
<211> LENGTH: 120
<212> TYPE: PRT
<213> ORGANISM: Mus musculus
<220> FEATURE:
<221> NAME/KEY: CDRH1
<222> LOCATION: (26)..(35)
<220> FEATURE:
<221> NAME/KEY: CDRH2
```

```
<222> LOCATION: (50)..(66)
<220> FEATURE:
<221> NAME/KEY: CDRH3
<222> LOCATION: (99)..(109)

<400> SEQUENCE: 4

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Ala Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Ser Asp Asp Phe
50                  55                  60

Lys Gly Arg Phe Ala Phe Ser Leu Glu Thr Ser Ala Asn Thr Ala Tyr
65                  70                  75                  80

Leu Gln Ile Asn Asn Leu Lys Asn Glu Asp Thr Ala Ala Tyr Phe Cys
                85                  90                  95

Thr Arg Gly Gly Gly Tyr Asp Glu Asp Tyr Phe Asp Tyr Trp Gly Gln
            100                 105                 110

Gly Thr Thr Leu Thr Val Ser Ser
        115                 120

<210> SEQ ID NO 5
<211> LENGTH: 119
<212> TYPE: PRT
<213> ORGANISM: Mus musculus
<220> FEATURE:
<221> NAME/KEY: CDRH1
<222> LOCATION: (26)..(35)
<220> FEATURE:
<221> NAME/KEY: CDRH2
<222> LOCATION: (50)..(66)
<220> FEATURE:
<221> NAME/KEY: CDRH3
<222> LOCATION: (99)..(108)

<400> SEQUENCE: 5

Gln Val Pro Leu Gln Gln Pro Gly Thr Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Ile His Trp Val Lys Gln Arg Pro Glu Gln Gly Leu Glu Trp Ile
        35                  40                  45

Gly Glu Ile Asp Pro Ser Asp Ser Tyr Thr Tyr Tyr Asn Gln Lys Phe
50                  55                  60

Lys Asp Lys Ala Thr Leu Thr Val Asp Lys Ser Ser Thr Thr Ala Phe
65                  70                  75                  80

Leu Gln Leu Ser Ser Leu Thr Ser Glu Asp Ser Ala Val Tyr Tyr Cys
                85                  90                  95

Ala Arg Ser Leu Tyr Asp Tyr Asp Gly Val Pro Asp Trp Gly Gln Gly
            100                 105                 110

Thr Leu Val Thr Val Ser Ala
        115

<210> SEQ ID NO 6
<211> LENGTH: 108
<212> TYPE: PRT
<213> ORGANISM: Rattus norvegicus
<220> FEATURE:
<221> NAME/KEY: CDRL1
<222> LOCATION: (24)..(34)
```

```
<220> FEATURE:
<221> NAME/KEY: CDRL2
<222> LOCATION: (50)..(56)
<220> FEATURE:
<221> NAME/KEY: CDRL3
<222> LOCATION: (89)..(97)

<400> SEQUENCE: 6

Asp Ile Gln Met Thr Gln Ser Pro Ala Ser Leu Ser Ala Ser Leu Gly
1               5                   10                  15

Glu Thr Val Thr Ile Glu Cys Leu Ala Ser Glu Asp Ile Tyr Ser Asn
            20                  25                  30

Leu Ala Trp Tyr Gln Gln Lys Pro Gly Lys Ser Pro Gln Leu Leu Ile
        35                  40                  45

Tyr Tyr Ala Asn Ser Leu Asn Asp Gly Val Pro Ser Arg Phe Ser Gly
50                  55                  60

Ser Gly Ser Gly Thr Gln Tyr Ser Leu Lys Ile Asn Ser Leu Gln Ser
65                  70                  75                  80

Glu Asp Val Ser Ile Tyr Phe Cys Gln Gln Asn Tyr Tyr Ser Pro Pro
            85                  90                  95

Thr Phe Gly Gly Gly Thr Lys Leu Glu Leu Lys Arg
            100                 105

<210> SEQ ID NO 7
<211> LENGTH: 108
<212> TYPE: PRT
<213> ORGANISM: Rattus norvegicus
<220> FEATURE:
<221> NAME/KEY: CDRL1
<222> LOCATION: (24)..(34)
<220> FEATURE:
<221> NAME/KEY: CDRL2
<222> LOCATION: (50)..(56)
<220> FEATURE:
<221> NAME/KEY: CDRL3
<222> LOCATION: (89)..(97)

<400> SEQUENCE: 7

Asp Ile Gln Met Thr Gln Ser Pro Ala Ser Leu Ser Ala Ser Leu Gly
1               5                   10                  15

Glu Thr Val Ser Ile Glu Cys Leu Ala Ser Glu Asp Ile Tyr Asn Asn
            20                  25                  30

Leu Ala Trp Tyr Gln Gln Lys Pro Gly Lys Ser Pro Gln Leu Leu Ile
        35                  40                  45

Tyr His Ala Ser Leu Gln Asp Gly Val Pro Ser Arg Phe Ser Gly
50                  55                  60

Ser Gly Ser Gly Thr Gln Tyr Ser Leu Lys Ile Asn Ser Leu Glu Ser
65                  70                  75                  80

Glu Asp Ala Ala Thr Tyr Phe Cys Leu Gln Asp Ser Glu Tyr Pro Pro
            85                  90                  95

Thr Phe Gly Gly Gly Thr Lys Leu Glu Leu Lys Arg
            100                 105

<210> SEQ ID NO 8
<211> LENGTH: 108
<212> TYPE: PRT
<213> ORGANISM: Rattus norvegicus
<220> FEATURE:
<221> NAME/KEY: CDRL1
<222> LOCATION: (24)..(34)
<220> FEATURE:
<221> NAME/KEY: CDRL2
<222> LOCATION: (50)..(56)
<220> FEATURE:
```

```
<221> NAME/KEY: CDRL3
<222> LOCATION: (89)..(97)

<400> SEQUENCE: 8

Asp Ile Val Met Thr Gln Ser Pro Thr Ser Met Ser Ile Ser Leu Gly
1               5                   10                  15

Asp Arg Val Thr Met Asn Cys Lys Ala Ser Gln Asn Val Gly Ser Asn
            20                  25                  30

Val Asp Trp Tyr Gln Gln Lys Thr Gly Gln Ser Pro Lys Leu Leu Ile
        35                  40                  45

Tyr Lys Ala Ser Asn Arg Tyr Thr Gly Val Pro Asp Arg Phe Thr Gly
50                  55                  60

Ser Gly Ser Gly Thr Asp Phe Thr Phe Thr Ile Ser Asn Met Gln Ala
65                  70                  75                  80

Glu Asp Leu Ser Val Tyr Tyr Cys Met Gln Ser Asn Ser Tyr Pro Leu
                85                  90                  95

Thr Phe Gly Ser Gly Thr Lys Leu Glu Ile Lys Arg
            100                 105

<210> SEQ ID NO 9
<211> LENGTH: 114
<212> TYPE: PRT
<213> ORGANISM: Mus musculus
<220> FEATURE:
<221> NAME/KEY: CDRL1
<222> LOCATION: (24)..(40)
<220> FEATURE:
<221> NAME/KEY: CDRL2
<222> LOCATION: (56)..(62)
<220> FEATURE:
<221> NAME/KEY: CDRL3
<222> LOCATION: (95)..(103)

<400> SEQUENCE: 9

Asp Ile Val Met Thr Gln Ser Pro Ser Ser Leu Ala Met Ser Val Gly
1               5                   10                  15

Gln Lys Val Thr Met Asn Cys Lys Ser Ser Gln Ser Leu Phe Asn Ser
            20                  25                  30

Ile Asn Gln Lys Thr Tyr Leu Ala Trp Tyr Gln Gln Arg Pro Gly Gln
        35                  40                  45

Ser Pro Lys Leu Leu Val Tyr Phe Ala Ser Thr Arg Glu Ser Gly Val
50                  55                  60

Pro Asp Arg Phe Ile Gly Ser Gly Ser Gly Thr Asp Phe Thr Leu Thr
65                  70                  75                  80

Ile Asn Ser Val Gln Ala Glu Asp Leu Ala Asp Tyr Phe Cys Gln Gln
                85                  90                  95

His Tyr Asp Thr Pro Trp Thr Phe Gly Gly Gly Thr Lys Leu Glu Ile
            100                 105                 110

Lys Arg

<210> SEQ ID NO 10
<211> LENGTH: 108
<212> TYPE: PRT
<213> ORGANISM: Mus musculus
<220> FEATURE:
<221> NAME/KEY: CDRL1
<222> LOCATION: (24)..(34)
<220> FEATURE:
<221> NAME/KEY: CDRL2
<222> LOCATION: (50)..(56)
<220> FEATURE:
<221> NAME/KEY: CDRL3
<222> LOCATION: (89)..(97)
```

```
<400> SEQUENCE: 10

Asp Ile Leu Met Thr Gln Ser Pro Ser Ser Met Ser Val Ser Leu Gly
1               5                   10                  15

Asp Thr Val Ser Ile Thr Cys His Ala Ser Gln Gly Ile Asp Asn Asn
                20                  25                  30

Ile Gly Trp Leu Gln Gln Lys Pro Gly Lys Ser Phe Lys Gly Leu Ile
            35                  40                  45

Tyr His Gly Thr Asn Leu Glu Asp Gly Val Pro Ser Arg Phe Ser Gly
50                  55                  60

Ser Gly Ser Gly Thr Asp Tyr Ser Leu Thr Ile Ser Ser Leu Glu Ser
65                  70                  75                  80

Glu Asp Phe Ala Asp Tyr Tyr Cys Val Gln Tyr Ala Gln Phe Pro Phe
                85                  90                  95

Thr Phe Gly Gly Gly Thr Lys Leu Glu Ile Arg Arg
            100                 105

<210> SEQ ID NO 11
<211> LENGTH: 10
<212> TYPE: PRT
<213> ORGANISM: Rattus norvegicus

<400> SEQUENCE: 11

Gly Phe Thr Phe Asn Asn Ser Trp Met Thr
1               5                   10

<210> SEQ ID NO 12
<211> LENGTH: 10
<212> TYPE: PRT
<213> ORGANISM: Rattus norvegicus

<400> SEQUENCE: 12

Gly Phe Asp Phe Asn Ser Tyr Gly Met Ser
1               5                   10

<210> SEQ ID NO 13
<211> LENGTH: 12
<212> TYPE: PRT
<213> ORGANISM: Rattus norvegicus

<400> SEQUENCE: 13

Gly Phe Ser Leu Ser Thr Tyr Gly Met Gly Val Gly
1               5                   10

<210> SEQ ID NO 14
<211> LENGTH: 10
<212> TYPE: PRT
<213> ORGANISM: Mus musculus

<400> SEQUENCE: 14

Gly Tyr Thr Phe Thr Asn Tyr Ala Met Asn
1               5                   10

<210> SEQ ID NO 15
<211> LENGTH: 10
<212> TYPE: PRT
<213> ORGANISM: Mus musculus

<400> SEQUENCE: 15

Gly Tyr Thr Phe Thr Ser Tyr Trp Ile His
1               5                   10
```

```
<210> SEQ ID NO 16
<211> LENGTH: 17
<212> TYPE: PRT
<213> ORGANISM: Rattus norvegicus

<400> SEQUENCE: 16

Ser Ile Thr Asn Thr Gly Gly Ser Thr Tyr Tyr Pro Asp Ser Val Lys
1               5                   10                  15
Gly

<210> SEQ ID NO 17
<211> LENGTH: 19
<212> TYPE: PRT
<213> ORGANISM: Rattus norvegicus

<400> SEQUENCE: 17

Asp Ile Asn Ser Lys Ser Tyr Asn Tyr Ala Thr Tyr Tyr Ala Asp Ser
1               5                   10                  15
Val Lys Asp

<210> SEQ ID NO 18
<211> LENGTH: 16
<212> TYPE: PRT
<213> ORGANISM: Rattus norvegicus

<400> SEQUENCE: 18

Asn Ile Trp Trp Asp Asp Lys Tyr Tyr Asn Pro Ser Leu Lys Asn
1               5                   10                  15

<210> SEQ ID NO 19
<211> LENGTH: 17
<212> TYPE: PRT
<213> ORGANISM: Mus musculus

<400> SEQUENCE: 19

Trp Ile Asn Thr Tyr Thr Gly Glu Pro Thr Tyr Ser Asp Asp Phe Lys
1               5                   10                  15
Gly

<210> SEQ ID NO 20
<211> LENGTH: 17
<212> TYPE: PRT
<213> ORGANISM: Mus musculus

<400> SEQUENCE: 20

Glu Ile Asp Pro Ser Asp Ser Tyr Thr Tyr Tyr Asn Gln Lys Phe Lys
1               5                   10                  15
Asp

<210> SEQ ID NO 21
<211> LENGTH: 8
<212> TYPE: PRT
<213> ORGANISM: Rattus norvegicus

<400> SEQUENCE: 21

Glu Asp Asn Ser Gly Tyr Asp Tyr
1               5

<210> SEQ ID NO 22
<211> LENGTH: 8
<212> TYPE: PRT
<213> ORGANISM: Rattus norvegicus

<400> SEQUENCE: 22
```

```
His His Ser Asp Tyr Phe Glu Tyr
1               5

<210> SEQ ID NO 23
<211> LENGTH: 18
<212> TYPE: PRT
<213> ORGANISM: Rattus norvegicus

<400> SEQUENCE: 23

Ile Asp Ala His Pro Met Gly Ile Thr Thr Pro Asp Tyr Tyr Val Val
1               5                   10                  15

Asp Ala

<210> SEQ ID NO 24
<211> LENGTH: 11
<212> TYPE: PRT
<213> ORGANISM: Mus musculus

<400> SEQUENCE: 24

Gly Gly Gly Tyr Asp Glu Asp Tyr Phe Asp Tyr
1               5                   10

<210> SEQ ID NO 25
<211> LENGTH: 10
<212> TYPE: PRT
<213> ORGANISM: Mus musculus

<400> SEQUENCE: 25

Ser Leu Tyr Asp Tyr Asp Gly Val Pro Asp
1               5                   10

<210> SEQ ID NO 26
<211> LENGTH: 11
<212> TYPE: PRT
<213> ORGANISM: Rattus norvegicus

<400> SEQUENCE: 26

Leu Ala Ser Glu Asp Ile Tyr Ser Asn Leu Ala
1               5                   10

<210> SEQ ID NO 27
<211> LENGTH: 11
<212> TYPE: PRT
<213> ORGANISM: Rattus norvegicus

<400> SEQUENCE: 27

Leu Ala Ser Glu Asp Ile Tyr Asn Asn Leu Ala
1               5                   10

<210> SEQ ID NO 28
<211> LENGTH: 11
<212> TYPE: PRT
<213> ORGANISM: Rattus norvegicus

<400> SEQUENCE: 28

Lys Ala Ser Gln Asn Val Gly Ser Asn Val Asp
1               5                   10

<210> SEQ ID NO 29
<211> LENGTH: 17
<212> TYPE: PRT
<213> ORGANISM: Mus musculus

<400> SEQUENCE: 29
```

```
Lys Ser Ser Gln Ser Leu Phe Asn Ser Ile Asn Gln Lys Thr Tyr Leu
1               5                   10                  15

Ala

<210> SEQ ID NO 30
<211> LENGTH: 11
<212> TYPE: PRT
<213> ORGANISM: Mus musculus

<400> SEQUENCE: 30

His Ala Ser Gln Gly Ile Asp Asn Asn Ile Gly
1               5                   10

<210> SEQ ID NO 31
<211> LENGTH: 7
<212> TYPE: PRT
<213> ORGANISM: Rattus norvegicus

<400> SEQUENCE: 31

Tyr Ala Asn Ser Leu Asn Asp
1               5

<210> SEQ ID NO 32
<211> LENGTH: 7
<212> TYPE: PRT
<213> ORGANISM: Rattus norvegicus

<400> SEQUENCE: 32

His Ala Ser Ser Leu Gln Asp
1               5

<210> SEQ ID NO 33
<211> LENGTH: 7
<212> TYPE: PRT
<213> ORGANISM: Rattus norvegicus

<400> SEQUENCE: 33

Lys Ala Ser Asn Arg Tyr Thr
1               5

<210> SEQ ID NO 34
<211> LENGTH: 7
<212> TYPE: PRT
<213> ORGANISM: Mus musculus

<400> SEQUENCE: 34

Phe Ala Ser Thr Arg Glu Ser
1               5

<210> SEQ ID NO 35
<211> LENGTH: 7
<212> TYPE: PRT
<213> ORGANISM: Mus musculus

<400> SEQUENCE: 35

His Gly Thr Asn Leu Glu Asp
1               5

<210> SEQ ID NO 36
<211> LENGTH: 9
<212> TYPE: PRT
<213> ORGANISM: Rattus norvegicus

<400> SEQUENCE: 36

Gln Gln Asn Tyr Tyr Ser Pro Pro Thr
```

```
<210> SEQ ID NO 37
<211> LENGTH: 9
<212> TYPE: PRT
<213> ORGANISM: Rattus norvegicus

<400> SEQUENCE: 37

Leu Gln Asp Ser Glu Tyr Pro Pro Thr
1               5

<210> SEQ ID NO 38
<211> LENGTH: 9
<212> TYPE: PRT
<213> ORGANISM: Rattus norvegicus

<400> SEQUENCE: 38

Met Gln Ser Asn Ser Tyr Pro Leu Thr
1               5

<210> SEQ ID NO 39
<211> LENGTH: 9
<212> TYPE: PRT
<213> ORGANISM: Mus musculus

<400> SEQUENCE: 39

Gln Gln His Tyr Asp Thr Pro Trp Thr
1               5

<210> SEQ ID NO 40
<211> LENGTH: 9
<212> TYPE: PRT
<213> ORGANISM: Mus musculus

<400> SEQUENCE: 40

Val Gln Tyr Ala Gln Phe Pro Phe Thr
1               5

<210> SEQ ID NO 41
<211> LENGTH: 629
<212> TYPE: PRT
<213> ORGANISM: Homo sapiens
<220> FEATURE:
<221> NAME/KEY: SIGNAL
<222> LOCATION: (1)..(23)

<400> SEQUENCE: 41

Met Asn Gln Val Thr Ile Gln Trp Asp Ala Val Ile Ala Leu Tyr Ile
1               5                   10                  15

Leu Phe Ser Trp Cys His Gly Gly Ile Thr Asn Ile Asn Cys Ser Gly
            20                  25                  30

His Ile Trp Val Glu Pro Ala Thr Ile Phe Lys Met Gly Met Asn Ile
        35                  40                  45

Ser Ile Tyr Cys Gln Ala Ala Ile Lys Asn Cys Gln Pro Arg Lys Leu
    50                  55                  60

His Phe Tyr Lys Asn Gly Ile Lys Glu Arg Phe Gln Ile Thr Arg Ile
65                  70                  75                  80

Asn Lys Thr Thr Ala Arg Leu Trp Tyr Lys Asn Phe Leu Glu Pro His
                85                  90                  95

Ala Ser Met Tyr Cys Thr Ala Glu Cys Pro Lys His Phe Gln Glu Thr
            100                 105                 110

Leu Ile Cys Gly Lys Asp Ile Ser Ser Gly Tyr Pro Pro Asp Ile Pro
        115                 120                 125
```

```
Asp Glu Val Thr Cys Val Ile Tyr Glu Tyr Ser Gly Asn Met Thr Cys
    130                 135                 140

Thr Trp Asn Ala Gly Lys Leu Thr Tyr Ile Asp Thr Lys Tyr Val Val
145                 150                 155                 160

His Val Lys Ser Leu Glu Thr Glu Glu Gln Gln Tyr Leu Thr Ser
            165                 170                 175

Ser Tyr Ile Asn Ile Ser Thr Asp Ser Leu Gln Gly Gly Lys Lys Tyr
            180                 185                 190

Leu Val Trp Val Gln Ala Ala Asn Ala Leu Gly Met Glu Glu Ser Lys
        195                 200                 205

Gln Leu Gln Ile His Leu Asp Asp Ile Val Ile Pro Ser Ala Ala Val
    210                 215                 220

Ile Ser Arg Ala Glu Thr Ile Asn Ala Thr Val Pro Lys Thr Ile Ile
225                 230                 235                 240

Tyr Trp Asp Ser Gln Thr Thr Ile Glu Lys Val Ser Cys Glu Met Arg
            245                 250                 255

Tyr Lys Ala Thr Thr Asn Gln Thr Trp Asn Val Lys Glu Phe Asp Thr
            260                 265                 270

Asn Phe Thr Tyr Val Gln Gln Ser Glu Phe Tyr Leu Glu Pro Asn Ile
        275                 280                 285

Lys Tyr Val Phe Gln Val Arg Cys Gln Glu Thr Gly Lys Arg Tyr Trp
    290                 295                 300

Gln Pro Trp Ser Ser Pro Phe Phe His Lys Thr Pro Glu Thr Val Pro
305                 310                 315                 320

Gln Val Thr Ser Lys Ala Phe Gln His Asp Thr Trp Asn Ser Gly Leu
            325                 330                 335

Thr Val Ala Ser Ile Ser Thr Gly His Leu Thr Ser Asp Asn Arg Gly
            340                 345                 350

Asp Ile Gly Leu Leu Leu Gly Met Ile Val Phe Ala Val Met Leu Ser
        355                 360                 365

Ile Leu Ser Leu Ile Gly Ile Phe Asn Arg Ser Phe Arg Thr Gly Ile
    370                 375                 380

Lys Arg Arg Ile Leu Leu Leu Ile Pro Lys Trp Leu Tyr Glu Asp Ile
385                 390                 395                 400

Pro Asn Met Lys Asn Ser Asn Val Val Lys Met Leu Gln Glu Asn Ser
            405                 410                 415

Glu Leu Met Asn Asn Asn Ser Ser Glu Gln Val Leu Tyr Val Asp Pro
            420                 425                 430

Met Ile Thr Glu Ile Lys Glu Ile Phe Ile Pro Glu His Lys Pro Thr
        435                 440                 445

Asp Tyr Lys Lys Glu Asn Thr Gly Pro Leu Glu Thr Arg Asp Tyr Pro
    450                 455                 460

Gln Asn Ser Leu Phe Asp Asn Thr Thr Val Val Tyr Ile Pro Asp Leu
465                 470                 475                 480

Asn Thr Gly Tyr Lys Pro Gln Ile Ser Asn Phe Leu Pro Glu Gly Ser
            485                 490                 495

His Leu Ser Asn Asn Asn Glu Ile Thr Ser Leu Thr Leu Lys Pro Pro
            500                 505                 510

Val Asp Ser Leu Asp Ser Gly Asn Asn Pro Arg Leu Gln Lys His Pro
        515                 520                 525

Asn Phe Ala Phe Ser Val Ser Ser Val Asn Ser Leu Ser Asn Thr Ile
    530                 535                 540

Phe Leu Gly Glu Leu Ser Leu Ile Leu Asn Gln Gly Glu Cys Ser Ser
```

-continued

```
            545                 550                 555                 560
Pro Asp Ile Gln Asn Ser Val Glu Glu Thr Thr Met Leu Leu Glu
                565                 570                 575

Asn Asp Ser Pro Ser Glu Thr Ile Pro Glu Gln Thr Leu Leu Pro Asp
                580                 585                 590

Glu Phe Val Ser Cys Leu Gly Ile Val Asn Glu Glu Leu Pro Ser Ile
                595                 600                 605

Asn Thr Tyr Phe Pro Gln Asn Ile Leu Glu Ser His Phe Asn Arg Ile
                610                 615                 620

Ser Leu Leu Glu Lys
625

<210> SEQ ID NO 42
<211> LENGTH: 644
<212> TYPE: PRT
<213> ORGANISM: Mus musculus
<220> FEATURE:
<221> NAME/KEY: SIGNAL
<222> LOCATION: (1)..(23)

<400> SEQUENCE: 42

Met Ser His Leu Thr Leu Gln Leu His Val Ile Ala Leu Tyr Val
1               5                   10                  15

Leu Phe Arg Trp Cys His Gly Gly Ile Thr Ser Ile Asn Cys Ser Gly
                20                  25                  30

Asp Met Trp Val Glu Pro Gly Glu Ile Phe Gln Met Gly Met Asn Val
                35                  40                  45

Ser Ile Tyr Cys Gln Glu Ala Leu Lys His Cys Arg Pro Arg Asn Leu
50                  55                  60

Tyr Phe Tyr Lys Asn Gly Phe Lys Glu Phe Asp Ile Thr Arg Ile
65                  70                  75                  80

Asn Arg Thr Thr Ala Arg Ile Trp Tyr Lys Gly Phe Ser Glu Pro His
                85                  90                  95

Ala Tyr Met His Cys Thr Ala Glu Cys Pro Gly His Phe Gln Glu Thr
                100                 105                 110

Leu Ile Cys Gly Lys Asp Ile Ser Ser Gly His Pro Pro Asp Ala Pro
                115                 120                 125

Ser Asn Leu Thr Cys Val Ile Tyr Glu Tyr Ser Gly Asn Met Thr Cys
130                 135                 140

Thr Trp Asn Thr Gly Lys Pro Thr Tyr Ile Asp Thr Lys Tyr Ile Val
145                 150                 155                 160

His Val Lys Ser Leu Glu Thr Glu Glu Gln Gln Tyr Leu Ala Ser
                165                 170                 175

Ser Tyr Val Lys Ile Ser Thr Asp Ser Leu Gln Gly Ser Arg Lys Tyr
                180                 185                 190

Leu Val Trp Val Gln Ala Val Asn Ser Leu Gly Met Glu Asn Ser Gln
                195                 200                 205

Gln Leu His Val His Leu Asp Asp Ile Val Ile Pro Ser Ala Ser Ile
                210                 215                 220

Ile Ser Arg Ala Glu Thr Thr Asn Asp Thr Val Pro Lys Thr Ile Val
225                 230                 235                 240

Tyr Trp Lys Ser Lys Thr Met Ile Glu Lys Val Phe Cys Glu Met Arg
                245                 250                 255

Tyr Lys Thr Thr Thr Asn Gln Thr Trp Ser Val Lys Glu Phe Asp Ala
                260                 265                 270

Asn Phe Thr Tyr Val Gln Gln Ser Glu Phe Tyr Leu Glu Pro Asp Ser
```

|     |     |     |     |     |     |     |     |     |     |     |     |     |     |     |
|---|---|---|---|---|---|---|---|---|---|---|---|---|---|---|
|     |     | 275 |     |     |     | 280 |     |     |     | 285 |     |     |     |     |

Lys Tyr Val Phe Gln Val Arg Cys Gln Glu Thr Gly Lys Arg Asn Trp
290                 295                 300

Gln Pro Trp Ser Ser Pro Phe Val His Gln Thr Ser Gln Glu Thr Gly
305                 310                 315                 320

Lys Arg Asn Trp Gln Pro Trp Ser Ser Pro Phe Val His Gln Thr Ser
            325                 330                 335

Gln Thr Val Ser Gln Val Thr Ala Lys Ser Ser His Glu Pro Gln Lys
            340                 345                 350

Met Glu Met Leu Ser Ala Thr Ile Phe Arg Gly His Pro Ala Ser Gly
            355                 360                 365

Asn His Gln Asp Ile Gly Leu Leu Ser Gly Met Val Phe Leu Ala Ile
370                 375                 380

Met Leu Pro Ile Phe Ser Leu Ile Gly Ile Phe Asn Arg Ser Leu Arg
385                 390                 395                 400

Ile Gly Ile Lys Arg Lys Val Leu Leu Met Ile Pro Lys Trp Leu Tyr
            405                 410                 415

Glu Asp Ile Pro Asn Met Glu Asn Ser Asn Val Ala Lys Leu Leu Gln
            420                 425                 430

Glu Lys Ser Val Phe Glu Asn Asp Asn Ala Ser Glu Gln Ala Leu Tyr
            435                 440                 445

Val Asp Pro Val Leu Thr Glu Ile Ser Glu Ile Pro Leu Glu His
450                 455                 460

Lys Pro Thr Asp Tyr Lys Glu Arg Leu Thr Gly Leu Leu Glu Thr
465                 470                 475                 480

Arg Asp Cys Pro Leu Gly Met Leu Ser Thr Ser Ser Val Val Tyr
            485                 490                 495

Ile Pro Asp Leu Asn Thr Gly Tyr Lys Pro Gln Val Ser Asn Val Pro
            500                 505                 510

Pro Gly Gly Asn Leu Phe Ile Asn Arg Asp Glu Arg Asp Pro Thr Ser
            515                 520                 525

Leu Glu Thr Thr Asp Asp His Phe Ala Arg Leu Lys Thr Tyr Pro Asn
530                 535                 540

Phe Gln Phe Ser Ala Ser Ser Met Ala Leu Leu Asn Lys Thr Leu Ile
545                 550                 555                 560

Leu Asp Glu Leu Cys Leu Val Leu Asn Gln Gly Glu Phe Asn Ser Leu
            565                 570                 575

Asp Ile Lys Asn Ser Arg Gln Glu Glu Thr Ser Ile Val Leu Gln Ser
            580                 585                 590

Asp Ser Pro Ser Glu Thr Ile Pro Ala Gln Thr Leu Leu Ser Asp Glu
            595                 600                 605

Phe Val Ser Cys Leu Ala Ile Gly Asn Glu Asp Leu Pro Ser Ile Asn
610                 615                 620

Ser Tyr Phe Pro Gln Asn Val Leu Glu Ser His Phe Ser Arg Ile Ser
625                 630                 635                 640

Leu Phe Gln Lys

<210> SEQ ID NO 43
<211> LENGTH: 662
<212> TYPE: PRT
<213> ORGANISM: Homo sapiens
<220> FEATURE:
<221> NAME/KEY: SIGNAL
<222> LOCATION: (1)..(24)

<400> SEQUENCE: 43

-continued

```
Met Glu Pro Leu Val Thr Trp Val Pro Leu Leu Phe Leu Phe Leu
1               5                   10                  15

Leu Ser Arg Gln Gly Ala Ala Cys Arg Thr Ser Glu Cys Cys Phe Gln
            20                  25                  30

Asp Pro Pro Tyr Pro Asp Ala Asp Ser Gly Ser Ala Ser Gly Pro Arg
                35                  40                  45

Asp Leu Arg Cys Tyr Arg Ile Ser Ser Asp Arg Tyr Glu Cys Ser Trp
        50                  55                  60

Gln Tyr Glu Gly Pro Thr Ala Gly Val Ser His Phe Leu Arg Cys Cys
65                  70                  75                  80

Leu Ser Ser Gly Arg Cys Cys Tyr Phe Ala Ala Gly Ser Ala Thr Arg
                85                  90                  95

Leu Gln Phe Ser Asp Gln Ala Gly Val Ser Val Leu Tyr Thr Val Thr
                100                 105                 110

Leu Trp Val Glu Ser Trp Ala Arg Asn Gln Thr Glu Lys Ser Pro Glu
        115                 120                 125

Val Thr Leu Gln Leu Tyr Asn Ser Val Lys Tyr Glu Pro Pro Leu Gly
    130                 135                 140

Asp Ile Lys Val Ser Lys Leu Ala Gly Gln Leu Arg Met Glu Trp Glu
145                 150                 155                 160

Thr Pro Asp Asn Gln Val Gly Ala Glu Val Gln Phe Arg His Arg Thr
                165                 170                 175

Pro Ser Ser Pro Trp Lys Leu Gly Asp Cys Gly Pro Gln Asp Asp Asp
                180                 185                 190

Thr Glu Ser Cys Leu Cys Pro Leu Glu Met Asn Val Ala Gln Glu Phe
            195                 200                 205

Gln Leu Arg Arg Arg Gln Leu Gly Ser Gln Gly Ser Ser Trp Ser Lys
        210                 215                 220

Trp Ser Ser Pro Val Cys Val Pro Pro Glu Asn Pro Pro Gln Pro Gln
225                 230                 235                 240

Val Arg Phe Ser Val Glu Gln Leu Gly Gln Asp Gly Arg Arg Arg Leu
                245                 250                 255

Thr Leu Lys Glu Gln Pro Thr Gln Leu Glu Leu Pro Glu Gly Cys Gln
            260                 265                 270

Gly Leu Ala Pro Gly Thr Glu Val Thr Tyr Arg Leu Gln Leu His Met
        275                 280                 285

Leu Ser Cys Pro Cys Lys Ala Lys Ala Thr Arg Thr Leu His Leu Gly
    290                 295                 300

Lys Met Pro Tyr Leu Ser Gly Ala Ala Tyr Asn Val Ala Val Ile Ser
305                 310                 315                 320

Ser Asn Gln Phe Gly Pro Gly Leu Asn Gln Thr Trp His Ile Pro Ala
                325                 330                 335

Asp Thr His Thr Glu Pro Val Ala Leu Asn Ile Ser Val Gly Thr Asn
            340                 345                 350

Gly Thr Thr Met Tyr Trp Pro Ala Arg Ala Gln Ser Met Thr Tyr Cys
        355                 360                 365

Ile Glu Trp Gln Pro Val Gly Gln Asp Gly Gly Leu Ala Thr Cys Ser
    370                 375                 380

Leu Thr Ala Pro Gln Asp Pro Asp Pro Ala Gly Met Ala Thr Tyr Ser
385                 390                 395                 400

Trp Ser Arg Glu Ser Gly Ala Met Gly Gln Glu Lys Cys Tyr Tyr Ile
                405                 410                 415

Thr Ile Phe Ala Ser Ala His Pro Glu Lys Leu Thr Leu Trp Ser Thr
```

-continued

```
                420             425             430
Val Leu Ser Thr Tyr His Phe Gly Gly Asn Ala Ser Ala Ala Gly Thr
            435                 440                 445

Pro His His Val Ser Val Lys Asn His Ser Leu Asp Ser Val Ser Val
        450                 455                 460

Asp Trp Ala Pro Ser Leu Leu Ser Thr Cys Pro Gly Val Leu Lys Glu
465                 470                 475                 480

Tyr Val Val Arg Cys Arg Asp Glu Asp Ser Lys Gln Val Ser Glu His
                485                 490                 495

Pro Val Gln Pro Thr Glu Thr Gln Val Thr Leu Ser Gly Leu Arg Ala
            500                 505                 510

Gly Val Ala Tyr Thr Val Gln Val Arg Ala Asp Thr Ala Trp Leu Arg
        515                 520                 525

Gly Val Trp Ser Gln Pro Gln Arg Phe Ser Ile Glu Val Gln Val Ser
    530                 535                 540

Asp Trp Leu Ile Phe Phe Ala Ser Leu Gly Ser Phe Leu Ser Ile Leu
545                 550                 555                 560

Leu Val Gly Val Leu Gly Tyr Leu Gly Leu Asn Arg Ala Ala Arg His
                565                 570                 575

Leu Cys Pro Pro Leu Pro Thr Pro Cys Ala Ser Ser Ala Ile Glu Phe
            580                 585                 590

Pro Gly Gly Lys Glu Thr Trp Gln Trp Ile Asn Pro Val Asp Phe Gln
        595                 600                 605

Glu Glu Ala Ser Leu Gln Glu Ala Leu Val Val Glu Met Ser Trp Asp
    610                 615                 620

Lys Gly Glu Arg Thr Glu Pro Leu Glu Lys Thr Glu Leu Pro Glu Gly
625                 630                 635                 640

Ala Pro Glu Leu Ala Leu Asp Thr Glu Leu Ser Leu Glu Asp Gly Asp
                645                 650                 655

Arg Cys Lys Ala Lys Met
            660

<210> SEQ ID NO 44
<211> LENGTH: 738
<212> TYPE: PRT
<213> ORGANISM: Mus musculus
<220> FEATURE:
<221> NAME/KEY: SIGNAL
<222> LOCATION: (1)..(19)

<400> SEQUENCE: 44

Met Asp Met Met Gly Leu Pro Gly Thr Ser Lys His Ile Thr Phe Leu
1               5                   10                  15

Leu Leu Cys Gln Leu Gly Ala Ser Gly Pro Gly Asp Gly Cys Cys Val
            20                  25                  30

Glu Lys Thr Ser Phe Pro Glu Gly Ala Ser Gly Ser Pro Leu Gly Pro
        35                  40                  45

Arg Asn Leu Ser Cys Tyr Arg Val Ser Lys Thr Asp Tyr Glu Cys Ser
    50                  55                  60

Trp Gln Tyr Asp Gly Pro Glu Asp Asn Val Ser His Val Leu Trp Cys
65                  70                  75                  80

Cys Phe Val Pro Pro Asn His Thr His Thr Gly Gln Glu Arg Cys Arg
                85                  90                  95

Tyr Phe Ser Ser Gly Pro Asp Arg Thr Val Gln Phe Trp Glu Gln Asp
            100                 105                 110

Gly Ile Pro Val Leu Ser Lys Val Asn Phe Trp Val Glu Ser Arg Leu
```

```
              115                 120                 125
Gly Asn Arg Thr Met Lys Ser Gln Lys Ile Ser Gln Tyr Leu Tyr Asn
    130                 135                 140

Trp Thr Lys Thr Thr Pro Pro Leu Gly His Ile Lys Val Ser Gln Ser
145                 150                 155                 160

His Gly Gln Leu Arg Met Asp Trp Asn Val Ser Glu Ala Gly Ala
                165                 170                 175

Glu Val Gln Phe Arg Arg Met Pro Thr Thr Asn Trp Thr Leu Gly
                180                 185                 190

Asp Cys Gly Pro Gln Val Asn Ser Gly Ser Gly Val Leu Gly Asp Ile
                195                 200                 205

Cys Gly Ser Met Ser Glu Ser Cys Leu Cys Pro Ser Glu Asn Met Ala
    210                 215                 220

Gln Glu Ile Gln Ile Arg Arg Arg Arg Leu Ser Ser Gly Ala Pro
225                 230                 235                 240

Gly Gly Pro Trp Ser Asp Trp Ser Met Pro Val Cys Val Pro Pro Glu
                245                 250                 255

Val Leu Pro Gln Ala Lys Ile Lys Phe Leu Val Glu Pro Leu Asn Gln
                260                 265                 270

Gly Gly Arg Arg Arg Leu Thr Met Gln Gly Gln Ser Pro Gln Leu Ala
                275                 280                 285

Val Pro Glu Gly Cys Arg Gly Arg Pro Gly Ala Gln Val Lys Lys His
                290                 295                 300

Leu Val Leu Val Arg Met Leu Ser Cys Arg Cys Gln Ala Gln Thr Ser
305                 310                 315                 320

Lys Thr Val Pro Leu Gly Lys Lys Leu Asn Leu Ser Gly Ala Thr Tyr
                325                 330                 335

Asp Leu Asn Val Leu Ala Lys Thr Arg Phe Gly Arg Ser Thr Ile Gln
                340                 345                 350

Lys Trp His Leu Pro Ala Gln Glu Leu Thr Glu Thr Arg Ala Leu Asn
                355                 360                 365

Val Ser Val Gly Gly Asn Met Thr Ser Met Gln Trp Ala Ala Gln Ala
370                 375                 380

Pro Gly Thr Thr Tyr Cys Leu Glu Trp Gln Pro Trp Phe Gln His Arg
385                 390                 395                 400

Asn His Thr His Cys Thr Leu Ile Val Pro Glu Glu Asp Pro Ala
                405                 410                 415

Lys Met Val Thr His Ser Trp Ser Ser Lys Pro Thr Leu Glu Gln Glu
                420                 425                 430

Glu Cys Tyr Arg Ile Thr Val Phe Ala Ser Lys Asn Pro Lys Asn Pro
                435                 440                 445

Met Leu Trp Ala Thr Val Leu Ser Ser Tyr Tyr Phe Gly Gly Asn Ala
    450                 455                 460

Ser Arg Ala Gly Thr Pro Arg His Val Ser Val Arg Asn Gln Thr Gly
465                 470                 475                 480

Asp Ser Val Ser Val Glu Trp Thr Ala Ser Gln Leu Ser Thr Cys Pro
                485                 490                 495

Gly Val Leu Thr Gln Tyr Val Val Arg Cys Glu Ala Glu Asp Gly Ala
                500                 505                 510

Trp Glu Ser Glu Trp Leu Val Pro Pro Thr Lys Thr Gln Val Thr Leu
                515                 520                 525

Asp Gly Leu Arg Ser Arg Val Met Tyr Lys Val Gln Val Arg Ala Asp
530                 535                 540
```

```
Thr Ala Arg Leu Pro Gly Ala Trp Ser His Pro Gln Arg Phe Ser Phe
545                 550                 555                 560

Glu Val Gln Ile Ser Arg Leu Ser Ile Ile Phe Ala Ser Leu Gly Ser
                565                 570                 575

Phe Ala Ser Val Leu Leu Val Gly Ser Leu Gly Tyr Ile Gly Leu Asn
            580                 585                 590

Arg Ala Ala Trp His Leu Cys Pro Pro Leu Pro Thr Pro Cys Gly Ser
        595                 600                 605

Thr Ala Val Glu Phe Pro Gly Ser Gln Gly Lys Gln Ala Trp Gln Trp
    610                 615                 620

Cys Asn Pro Glu Asp Phe Pro Glu Val Leu Tyr Pro Arg Asp Ala Leu
625                 630                 635                 640

Val Val Glu Met Pro Gly Asp Arg Gly Asp Gly Thr Glu Ser Pro Gln
                645                 650                 655

Ala Ala Pro Glu Cys Ala Leu Asp Thr Arg Arg Pro Leu Glu Thr Gln
            660                 665                 670

Arg Gln Arg Gln Val Gln Ala Leu Ser Glu Ala Arg Arg Leu Gly Leu
        675                 680                 685

Ala Arg Glu Asp Cys Pro Arg Gly Asp Leu Ala His Val Thr Leu Pro
    690                 695                 700

Leu Leu Leu Gly Gly Val Thr Gln Gly Ala Ser Val Leu Asp Asp Leu
705                 710                 715                 720

Trp Arg Thr His Lys Thr Ala Glu Pro Gly Pro Thr Leu Gly Gln
                725                 730                 735

Glu Ala

<210> SEQ ID NO 45
<211> LENGTH: 120
<212> TYPE: PRT
<213> ORGANISM: Artificial Sequence
<220> FEATURE:
<223> OTHER INFORMATION: Mouse CDRs and human frameworks
<220> FEATURE:
<221> NAME/KEY: CDRH1
<222> LOCATION: (26)..(35)
<220> FEATURE:
<221> NAME/KEY: CDRH2
<222> LOCATION: (50)..(66)
<220> FEATURE:
<221> NAME/KEY: CDRH3
<222> LOCATION: (99)..(109)

<400> SEQUENCE: 45

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Ala Met Asn Trp Val Arg Gln Ala Pro Gly Gln Gly Leu Glu Trp Met
            35                  40                  45

Gly Trp Ile Asn Thr Tyr Thr Gly Glu Pro Thr Tyr Asn Glu Lys Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Gly Gly Tyr Asp Glu Asp Tyr Phe Asp Tyr Trp Gly Gln
            100                 105                 110

Gly Thr Leu Val Thr Val Ser Ser
        115                 120
```

<210> SEQ ID NO 46
<211> LENGTH: 120
<212> TYPE: PRT
<213> ORGANISM: Artificial Sequence
<220> FEATURE:
<223> OTHER INFORMATION: Mouse CDRs and human frameworks with T72L
      substitution
<220> FEATURE:
<221> NAME/KEY: CDRH1
<222> LOCATION: (26)..(35)
<220> FEATURE:
<221> NAME/KEY: CDRH2
<222> LOCATION: (50)..(66)
<220> FEATURE:
<221> NAME/KEY: CDRH3
<222> LOCATION: (99)..(109)

<400> SEQUENCE: 46

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Ala Met Asn Trp Val Arg Gln Ala Pro Gly Gln Gly Leu Glu Trp Met
            35                  40                  45

Gly Trp Ile Asn Thr Tyr Thr Gly Glu Pro Thr Tyr Ser Asp Asp Phe
    50                  55                  60

Lys Gly Arg Val Thr Met Thr Leu Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Gly Gly Tyr Asp Glu Asp Tyr Phe Asp Tyr Trp Gly Gln
            100                 105                 110

Gly Thr Leu Val Thr Val Ser Ser
        115                 120

<210> SEQ ID NO 47
<211> LENGTH: 120
<212> TYPE: PRT
<213> ORGANISM: Artificial Sequence
<220> FEATURE:
<223> OTHER INFORMATION: Mouse CDRs and human frameworks with M70F and
      T72L substitutions
<220> FEATURE:
<221> NAME/KEY: CDRH1
<222> LOCATION: (26)..(35)
<220> FEATURE:
<221> NAME/KEY: CDRH2
<222> LOCATION: (50)..(66)
<220> FEATURE:
<221> NAME/KEY: CDRH3
<222> LOCATION: (99)..(109)

<400> SEQUENCE: 47

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Ala Met Asn Trp Val Arg Gln Ala Pro Gly Gln Gly Leu Glu Trp Met
            35                  40                  45

Gly Trp Ile Asn Thr Tyr Thr Gly Glu Pro Thr Tyr Ser Asp Asp Phe
    50                  55                  60

Lys Gly Arg Val Thr Phe Thr Leu Asp Thr Ser Thr Ser Thr Ala Tyr
65                  70                  75                  80

```
Met Glu Leu Arg Ser Leu Arg Ser Asp Asp Thr Ala Val Tyr Tyr Cys
            85                  90                  95

Ala Arg Gly Gly Gly Tyr Asp Glu Asp Tyr Phe Asp Tyr Trp Gly Gln
        100                 105                 110

Gly Thr Leu Val Thr Val Ser Ser
        115                 120

<210> SEQ ID NO 48
<211> LENGTH: 115
<212> TYPE: PRT
<213> ORGANISM: Artificial Sequence
<220> FEATURE:
<223> OTHER INFORMATION: Mouse CDRs and human frameworks (subgroup IV)
<220> FEATURE:
<221> NAME/KEY: CDRL1
<222> LOCATION: (24)..(40)
<220> FEATURE:
<221> NAME/KEY: CDRL2
<222> LOCATION: (56)..(62)
<220> FEATURE:
<221> NAME/KEY: CDRL3
<222> LOCATION: (95)..(103)

<400> SEQUENCE: 48

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Phe Asn Ser
            20                  25                  30

Ile Asn Gln Lys Thr Tyr Leu Ala Trp Tyr Gln Gln Lys Pro Gly Gln
        35                  40                  45

Pro Pro Lys Leu Leu Ile Tyr Phe Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Tyr Asp Thr Pro Trp Thr Phe Gly Gln Gly Thr Lys Val Glu Ile
            100                 105                 110

Lys Arg Thr
        115

<210> SEQ ID NO 49
<211> LENGTH: 115
<212> TYPE: PRT
<213> ORGANISM: Artificial Sequence
<220> FEATURE:
<223> OTHER INFORMATION: Mouse CDRs and human frameworks (subgroup II)
<220> FEATURE:
<221> NAME/KEY: CDRL1
<222> LOCATION: (24)..(40)
<220> FEATURE:
<221> NAME/KEY: CDRL2
<222> LOCATION: (56)..(62)
<220> FEATURE:
<221> NAME/KEY: CDRL3
<222> LOCATION: (95)..(103)

<400> SEQUENCE: 49

Asp Ile Val Met Thr Gln Ser Pro Leu Ser Leu Pro Val Thr Pro Gly
1               5                   10                  15

Glu Pro Ala Ser Ile Ser Cys Lys Ser Ser Gln Ser Leu Phe Asn Ser
            20                  25                  30

Ile Asn Gln Lys Thr Tyr Leu Ala Trp Tyr Leu Gln Lys Pro Gly Gln
        35                  40                  45
```

```
Ser Pro Gln Leu Leu Ile Tyr Phe Ala Ser Thr Arg Glu Ser Gly Val
 50                  55                  60

Pro Asp Arg Phe Ser Gly Ser Gly Ser Gly Thr Asp Phe Thr Leu Lys
 65                  70                  75                  80

Ile Ser Arg Val Glu Ala Glu Asp Val Gly Val Tyr Tyr Cys Gln Gln
                 85                  90                  95

His Tyr Asp Thr Pro Trp Thr Phe Gly Gln Gly Thr Lys Val Glu Ile
            100                 105                 110

Lys Arg Thr
        115

<210> SEQ ID NO 50
<211> LENGTH: 450
<212> TYPE: PRT
<213> ORGANISM: Artificial Sequence
<220> FEATURE:
<223> OTHER INFORMATION: Mouse CDRs and human frameworks with M70F and
      T72L substitutions
<220> FEATURE:
<221> NAME/KEY: CDRH1
<222> LOCATION: (26)..(35)
<220> FEATURE:
<221> NAME/KEY: CDRH2
<222> LOCATION: (50)..(66)
<220> FEATURE:
<221> NAME/KEY: CDRH3
<222> LOCATION: (99)..(109)

<400> SEQUENCE: 50

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Asn Tyr
                 20                  25                  30

Ala Met Asn Trp Val Arg Gln Ala Pro Gly Gln Gly Leu Glu Trp Met
             35                  40                  45

Gly Trp Ile Asn Thr Tyr Thr Gly Glu Pro Thr Tyr Ser Asp Asp Phe
         50                  55                  60

Lys Gly Arg Val Thr Phe Thr Leu Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Gly Gly Gly Tyr Asp Glu Asp Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
        210                 215                 220

Lys Thr His Thr Cys Pro Pro Cys Pro Ala Pro Glu Leu Leu Gly Gly
225                 230                 235                 240
```

```
Pro Ser Val Phe Leu Phe Pro Pro Lys Pro Lys Asp Thr Leu Met Ile
                245                 250                 255

Ser Arg Thr Pro Glu Val Thr Cys Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 51
<211> LENGTH: 220
<212> TYPE: PRT
<213> ORGANISM: Artificial Sequence
<220> FEATURE:
<223> OTHER INFORMATION: Mouse CDRs and human frameworks (subgroup II)
<220> FEATURE:
<221> NAME/KEY: CDRL1
<222> LOCATION: (24)..(40)
<220> FEATURE:
<221> NAME/KEY: CDRL2
<222> LOCATION: (56)..(62)
<220> FEATURE:
<221> NAME/KEY: CDRL3
<222> LOCATION: (95)..(103)

<400> SEQUENCE: 51

Asp Ile Val Met Thr Gln Ser Pro Leu Ser Leu Pro Val Thr Pro Gly
1               5                   10                  15

Glu Pro Ala Ser Ile Ser Cys Lys Ser Ser Gln Ser Leu Phe Asn Ser
            20                  25                  30

Ile Asn Gln Lys Thr Tyr Leu Ala Trp Tyr Leu Gln Lys Pro Gly Gln
        35                  40                  45

Ser Pro Gln Leu Leu Ile Tyr Phe Ala Ser Thr Arg Glu Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Gln Gln
                85                  90                  95

His Tyr Asp Thr Pro Trp Thr Phe Gly Gln Gly Thr Lys Val Glu Ile
```

-continued

```
                100                 105                 110
Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
            130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
            210                 215                 220

<210> SEQ ID NO 52
<211> LENGTH: 17
<212> TYPE: PRT
<213> ORGANISM: Artificial Sequence
<220> FEATURE:
<223> OTHER INFORMATION: Mus musculus with Thr at position 9 rather
      than Ser

<400> SEQUENCE: 52

Lys Ser Ser Gln Ser Leu Phe Asn Thr Ile Asn Gln Lys Thr Tyr Leu
1               5                   10                  15

Ala

<210> SEQ ID NO 53
<211> LENGTH: 115
<212> TYPE: PRT
<213> ORGANISM: Artificial Sequence
<220> FEATURE:
<223> OTHER INFORMATION: Mouse CDRs and human frameworks (subgroup II)
      with S32T substitution
<220> FEATURE:
<221> NAME/KEY: CDRL1
<222> LOCATION: (24)..(40)
<220> FEATURE:
<221> NAME/KEY: CDRL2
<222> LOCATION: (56)..(62)
<220> FEATURE:
<221> NAME/KEY: CDRL3
<222> LOCATION: (95)..(103)

<400> SEQUENCE: 53

Asp Ile Val Met Thr Gln Ser Pro Leu Ser Leu Pro Val Thr Pro Gly
1               5                   10                  15

Glu Pro Ala Ser Ile Ser Cys Lys Ser Ser Gln Ser Leu Phe Asn Thr
            20                  25                  30

Ile Asn Gln Lys Thr Tyr Leu Ala Trp Tyr Leu Gln Lys Pro Gly Gln
        35                  40                  45

Ser Pro Gln Leu Leu Ile Tyr Phe Ala Ser Thr Arg Glu Ser Gly Val
50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Gln Gln
                85                  90                  95

His Tyr Asp Thr Pro Trp Thr Phe Gly Gln Gly Thr Lys Val Glu Ile
            100                 105                 110
```

Lys Arg Thr
       115

<210> SEQ ID NO 54
<211> LENGTH: 220
<212> TYPE: PRT
<213> ORGANISM: Artificial Sequence
<220> FEATURE:
<223> OTHER INFORMATION: Mouse CDRs and human frameworks (subgroup II)
      with S32T substitution
<220> FEATURE:
<221> NAME/KEY: CDRL1
<222> LOCATION: (24)..(40)
<220> FEATURE:
<221> NAME/KEY: CDRL2
<222> LOCATION: (56)..(62)
<220> FEATURE:
<221> NAME/KEY: CDRL3
<222> LOCATION: (95)..(103)

<400> SEQUENCE: 54

Asp Ile Val Met Thr Gln Ser Pro Leu Ser Leu Pro Val Thr Pro Gly
1               5                   10                  15

Glu Pro Ala Ser Ile Ser Cys Lys Ser Ser Gln Ser Leu Phe Asn Thr
            20                  25                  30

Ile Asn Gln Lys Thr Tyr Leu Ala Trp Tyr Leu Gln Lys Pro Gly Gln
        35                  40                  45

Ser Pro Gln Leu Leu Ile Tyr Phe Ala Ser Thr Arg Glu Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Gln Gln
                85                  90                  95

His Tyr Asp Thr Pro Trp Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 55
<211> LENGTH: 1410
<212> TYPE: DNA
<213> ORGANISM: Artificial Sequence
<220> FEATURE:
<223> OTHER INFORMATION: Mouse CDRs and human frameworks with changes
      encoding M70F and T72L substitutions

<400> SEQUENCE: 55
atggccgtgc tgggcctgct gttctgcctg gtgaccttcc ccagctgcgt gctgtcccag      60
gtgcagctgg tgcagagcgg agccgaggtg aagaagccag cgccagcgt caaggtgtcc     120

```
tgcaaggcca gcggctacac cttcaccaac tacgccatga actgggtgcg gcaggcccct      180
ggacagggac tggaatggat gggctggatc aacacctaca ccggcgagcc cacctacagc      240
gacgacttca agggcagggt gaccttcacc ctggacacca gcaccagcac cgcctacatg      300
gaactgagaa gcctgagatc cgacgacacc gccgtgtact actgcgccag aggcggcgga      360
tacgacgagg actacttcga ctactgggga cagggcaccc tggtgaccgt gagcagcgct      420
agcaccaagg gcccagcgt gttccccctg gccccagca gcaagagcac ctctggcggc       480
acagctgccc tcggctgtct ggtgaaggac tactttcccg agcccgtgac cgtgtcctgg      540
aacagcggag ccctgacctc cggcgtgcac accttcccg ccgtgctgca gagcagcggc      600
ctgtacagcc tgagcagcgt ggtgacagtg cccagctcta gcctgggaac ccagacctac      660
atctgcaacg tgaaccacaa gcccagcaac accaaggtgg acaagaaggt ggagcccaag      720
agctgcgaca agacccacac ctgcccccc tgcccagctc cagaactcct gggcggaccc       780
tccgtgttcc tgttcccccc caagcccaag gacaccctga tgatcagcag gacccccgag      840
gtgacctgcg tggtggtgga cgtgagccac gaggacccag aggtgaagtt caactggtac      900
gtggacggcg tggaggtgca caacgccaag accaagccca gagaggaaca gtacaacagc      960
acctacaggg tggtgtccgt gctgaccgtg ctgcaccagg actggctgaa cggcaaagag     1020
tacaagtgca aggtctccaa caaggccctg ccagccccca tcgagaaaac catcagcaag     1080
gccaagggcc agccacggga gccccaggtg tacaccctgc cccctcccg ggacgagctg      1140 accaagaacc aggtgtccct gacatgcctg gtgaagggct cctacccag cgacatcgcc       1200 gtggagtggg agagcaacgg ccagcccgag aacaactaca gaccaccc cccagtgctg       1260 gacagcgacg gcagcttctt cctgtacagc aagctgaccg tggacaagag caggtggcag     1320
cagggcaacg tgttcagctg cagcgtgatg cacgaggccc tgcacaacca ctacacccag     1380
aagagcctga gcctgtcccc cggcaagtga                                      1410
```

<210> SEQ ID NO 56
<211> LENGTH: 720
<212> TYPE: DNA
<213> ORGANISM: Artificial Sequence
<220> FEATURE:
<223> OTHER INFORMATION: Mouse CDRs and human frameworks (group II) with S32T substitution

<400> SEQUENCE: 56

```
atggccccg tgcagctgct gggcctgctg gtgctgttcc tgcccgccat gagatgcgac       60
atcgtgatga cccagagccc cctgagcctg cccgtgaccc caggcgagcc cgccagcatc      120
agctgcaaga gcagccagag cctgttcaac accatcaacc agaaaaccta cctggcctgg      180
tatctgcaga gcccggcca gtccccccag ctgctgatct acttcgccag cacccgggag       240
agcggcgtgc ccgacaggtt cagcggcagc ggctccggca ccgacttcac cctgaagatc      300
agcagggtgg aggccgagga cgtgggcgtg tactactgcc agcagcacta cgacaccccc      360
tggaccttcg gccagggcac caaggtggag atcaagcgta cggtggctgc ccccagcgtg      420
ttcatcttcc cccccagcga cgagcagctg aagagcggca ccgccagcgt ggtgtgcctg      480
ctgaacaact tctacccccg ggaggccaag gtgcagtgga aggtggacaa cgccctgcag      540
agcggcaaca gccaggaaag cgtcaccgag caggacagca aggactccac ctacagcctg      600
agcagcaccc tgaccctgag caaggccgac tacgagaagc acaaggtgta cgcctgcgag      660
gtgacccacc agggcctgtc cagccccgtg accaagagct tcaacagggg cgagtgctga     720
```

```
<210> SEQ ID NO 57
<211> LENGTH: 119
<212> TYPE: PRT
<213> ORGANISM: Artificial Sequence
<220> FEATURE:
<223> OTHER INFORMATION: Rat CDRs and human frameworks

<400> SEQUENCE: 57

Gln Val Gln Leu Val Glu Ser Gly Gly Val Val Gln Pro Gly Arg
1               5                   10                  15

Ser Leu Arg Leu Ser Cys Ala Ala Ser Gly Phe Asp Phe Asn Ser Tyr
            20                  25                  30

Gly Met Ser Trp Val Arg Gln Ala Pro Gly Lys Gly Leu Glu Trp Val
        35                  40                  45

Ala Asp Ile Asn Ser Lys Ser Tyr Asn Tyr Ala Thr Tyr Tyr Ala Asp
    50                  55                  60

Ser Val Lys Asp Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg His His Ser Asp Tyr Phe Glu Tyr Trp Gly Gln Gly
            100                 105                 110

Thr Leu Val Thr Val Ser Ser
        115

<210> SEQ ID NO 58
<211> LENGTH: 108
<212> TYPE: PRT
<213> ORGANISM: Artificial Sequence
<220> FEATURE:
<223> OTHER INFORMATION: Rat CDRs and human frameworks

<400> SEQUENCE: 58

Asp Ile Gln Met Thr Gln Ser Pro Ser Ser Leu Ser Ala Ser Val Gly
1               5                   10                  15

Asp Arg Val Thr Ile Thr Cys Leu Ala Ser Glu Asp Ile Tyr Asn Asn
            20                  25                  30

Leu Ala Trp Tyr Gln Gln Lys Pro Gly Lys Ala Pro Lys Leu Leu Ile
        35                  40                  45

Tyr His Ala Ser Ser Leu Gln Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Ser Glu Tyr Pro Pro
                85                  90                  95

Thr Phe Gly Gln Gly Thr Lys Val Glu Ile Lys Arg
            100                 105
```